United States Patent
Huynh et al.

(10) Patent No.: US 9,940,683 B2
(45) Date of Patent: Apr. 10, 2018

(54) MANAGING A RISK OF A LIABILITY THAT IS INCURRED IF A SUBJECT TREATED FOR A CONDITION IS RETREATED WITHIN A SPECIFIED TIME PERIOD

(71) Applicant: Elwha LLC, Bellevue, WA (US)

(72) Inventors: Grace Hsu Huynh, Seattle, WA (US); Roderick A. Hyde, Redmond, WA (US); Eric C. Leuthardt, St. Louis, MO (US); Tony S. Pan, Cambridge, MA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 985 days.

(21) Appl. No.: 13/956,128

(22) Filed: Jul. 31, 2013

(65) Prior Publication Data
US 2015/0039324 A1    Feb. 5, 2015

(51) Int. Cl.
*G06Q 50/22*    (2018.01)
*G06Q 10/06*    (2012.01)
*G06Q 40/04*    (2012.01)

(52) U.S. Cl.
CPC ......... *G06Q 50/22* (2013.01); *G06Q 10/0635* (2013.01); *G06Q 40/04* (2013.01)

(58) Field of Classification Search
CPC .. G06Q 50/22; G06F 19/3431; G06F 19/3437
USPC ........................................................ 705/2–4
See application file for complete search history.

(56) References Cited

U.S. PATENT DOCUMENTS

| | | |
|---|---|---|
| 5,876,926 A | 3/1999 | Beecham |
| 5,890,129 A | 3/1999 | Spurgeon |
| 5,897,989 A | 4/1999 | Beecham |
| 6,088,677 A | 7/2000 | Spurgeon |
| 6,604,080 B1 | 8/2003 | Kern |
| 6,973,371 B1 | 12/2005 | Benouali |
| 7,315,842 B1 | 1/2008 | Wang |
| 7,630,986 B1 | 12/2009 | Herz et al. |
| 8,260,634 B1 | 9/2012 | Lawlor |
| 8,321,243 B1 | 11/2012 | Harris, Sr. et al. |
| 8,452,620 B1 | 5/2013 | Grundfest |
| 8,650,048 B1 | 2/2014 | Hopkins, III et al. |
| 8,666,788 B1 | 3/2014 | Syed |
| 8,781,952 B1 | 7/2014 | Biase |
| 2002/0128877 A1 | 9/2002 | Levit |

(Continued)

OTHER PUBLICATIONS

Kruse et al., Risk Factors for All-Cause Hospital Readmission Within 30 Days of Hospital Discharge, May 2013, www.jcomjournal.com, vol. 20, No. 5, pp. 203-214 (Year: 2013).*

(Continued)

*Primary Examiner* — Joy Chng
(74) *Attorney, Agent, or Firm* — Fogg & Powers LLC

(57) ABSTRACT

An embodiment of a risk-management method includes determining a risk that a subject treated for a condition will be retreated within a time period, and calculating, in response to a determined risk, a fee for taking an action if the subject is retreated within the time period. For example, such an embodiment may aid in managing a risk of a liability that may be incurred if a subject treated for a condition is retreated for the condition, for a complication arising from the condition or from the treatment of the condition, or for another reason, within a specified retreatment time period.

29 Claims, 15 Drawing Sheets

(56) References Cited

U.S. PATENT DOCUMENTS

| | | | |
|---|---|---|---|
| 2002/0194109 A1 | 12/2002 | Takeshi | |
| 2003/0028406 A1 | 2/2003 | Herz et al. | |
| 2003/0139948 A1* | 7/2003 | Strech | G06Q 40/00 705/4 |
| 2004/0039710 A1* | 2/2004 | McMillan | G06Q 10/04 705/400 |
| 2004/0167849 A1 | 8/2004 | Yass et al. | |
| 2005/0010453 A1 | 1/2005 | Terlizzi et al. | |
| 2005/0131740 A1 | 6/2005 | Massenzio et al. | |
| 2005/0171883 A1 | 8/2005 | Dundas et al. | |
| 2005/0203779 A1 | 9/2005 | Prieston | |
| 2005/0203831 A1 | 9/2005 | Prieston | |
| 2005/0278200 A1 | 12/2005 | Brawley et al. | |
| 2006/0074708 A1 | 4/2006 | Woods | |
| 2006/0247953 A1 | 11/2006 | Pollack et al. | |
| 2007/0027783 A1 | 2/2007 | Meyer | |
| 2007/0156453 A1 | 7/2007 | Frielinghaus et al. | |
| 2007/0162365 A1 | 7/2007 | Weinreb | |
| 2008/0015896 A1* | 1/2008 | Reynolds | G06Q 20/10 705/2 |
| 2008/0065427 A1 | 3/2008 | Helitzer et al. | |
| 2008/0077450 A1 | 3/2008 | Klippel | |
| 2008/0103841 A1 | 5/2008 | Lewis et al. | |
| 2008/0126128 A1 | 5/2008 | Markman | |
| 2008/0154647 A1 | 6/2008 | Ress | |
| 2008/0267954 A1 | 10/2008 | Margolin et al. | |
| 2008/0270286 A1 | 10/2008 | Wilson et al. | |
| 2009/0037345 A1 | 2/2009 | Barker et al. | |
| 2009/0069789 A1 | 3/2009 | Freyman et al. | |
| 2009/0089197 A1 | 4/2009 | Barker et al. | |
| 2009/0106054 A1 | 4/2009 | Sarel | |
| 2009/0119133 A1 | 5/2009 | Yeransian et al. | |
| 2009/0132299 A1 | 5/2009 | Patton | |
| 2009/0240612 A1 | 9/2009 | Hoffman | |
| 2009/0248450 A1 | 10/2009 | Fernandez | |
| 2010/0017315 A1 | 1/2010 | Hahn-Carlson | |
| 2010/0211405 A1 | 8/2010 | Lutnick et al. | |
| 2010/0211416 A1 | 8/2010 | Frank et al. | |
| 2011/0040577 A1 | 2/2011 | Ward | |
| 2011/0046985 A1 | 2/2011 | Raheman | |
| 2011/0077978 A1 | 3/2011 | Thomas et al. | |
| 2011/0087500 A1 | 4/2011 | McCallum et al. | |
| 2011/0137686 A1 | 6/2011 | Mott | |
| 2011/0182877 A1 | 7/2011 | Francois et al. | |
| 2011/0257992 A1 | 10/2011 | Scantland et al. | |
| 2011/0313788 A1* | 12/2011 | Amland | G06F 19/3431 705/3 |
| 2012/0041790 A1 | 2/2012 | Koziol | |
| 2012/0078815 A1 | 3/2012 | Rossi et al. | |
| 2012/0109693 A1 | 5/2012 | Smith | |
| 2012/0185409 A1 | 7/2012 | Coleman et al. | |
| 2012/0232935 A1 | 9/2012 | Voccola | |
| 2012/0271661 A1 | 10/2012 | Reynolds et al. | |
| 2012/0284061 A1 | 11/2012 | Collins et al. | |
| 2013/0073310 A1 | 3/2013 | Awdeh | |
| 2013/0083054 A1 | 4/2013 | Bayouk | |
| 2013/0144639 A1 | 6/2013 | Hu et al. | |
| 2013/0159025 A1 | 6/2013 | Olaniyan | |
| 2013/0218741 A1* | 8/2013 | Fenichel | G06Q 40/04 705/37 |
| 2013/0246078 A1 | 9/2013 | Omidi | |
| 2013/0282408 A1 | 10/2013 | Snyder et al. | |
| 2013/0290023 A1 | 10/2013 | Hight et al. | |
| 2014/0108057 A1 | 4/2014 | Daniels et al. | |
| 2014/0156558 A1 | 6/2014 | Hendrix | |
| 2014/0358582 A1 | 12/2014 | Kemp et al. | |
| 2015/0039337 A1 | 2/2015 | Huynh et al. | |
| 2015/0039486 A1 | 2/2015 | Huynh et al. | |

OTHER PUBLICATIONS

Delta Dental, Dental Benefits Handbook, 2011, pp. 1-33 (Year: 2011).*

Schilling, Falko ESQ.; "Denied Claims in Vermont"; Apr. 2, 2013; 5 pgs.; located at: http://www.vermontforsinglepayer.org.

Stein, Andrew; "New disclosures show MVP denied 15.5 percent of patient claims in 2012; Blue Cross denied 7.6 percent"; Vermont Health Care for All; downloaded Nov. 3, 2014 from website located at: http://www.vermontforsinglepayer.org/newdisclosuress howmvpdenied155percentofpatientclaimsin2012bluecrossdenied 76percent; 2 pgs.

"Resetting the Roadmap: Managing in a New Securities Lending Environment for Beneficial Asset Holders"; Office of Innovation Thought Leadership Series Third Quarter 2009; 16 pages; 2009; The Bank of New York Mellon Corporation.

Janet M Friedmann, Gordon L Jensen, Helen Smiciklas-Wright, and Mark A McCamish: "Predicting early nonelective hospital readmission in nutritionally compromised older adults", 1997 American Society for Clinical Nutrition, Am J Clin Nutr 1997;65: pp. 1714-1720. Printed in USA.

HCUPnet: A tool for identifying, tracking, and analyzing national hospital statistics; http://hcupnet.ahrq.gov/HCUPnet.jsp?Id=485C9DBC4B9A2A67&Form=MAINSEL&JS=Y &Action=%3E%3ENext%3E%3E&_MAINSEL=Readmission %20Summary%20Tables; 2 pages.

Jay G. Berry et al.: "Pediatric Readmission Prevalence and Variability Across Hospitals", JAMA, Jan. 23/30, 2013—vol. 309, No. 4; 2013 American Medical Association. Corrected on Feb. 6, 2013; Downloaded From: http://jama.jamanetwork.com/ on Nov. 3, 2014; 9 pages.

Kumar Dharmarajan et al.: "Diagnoses and Timing of 30-Day Readmissions After Hospitalization for Heart Failure, Acute Myocardial Infarction, or Pneumonia", JAMA, Jan. 23/30, 2013—vol. 309, No. 4, 2013 American Medical Association; Downloaded From: http://jama.jamanetwork.com/ on Nov. 3, 2014; 9 pages.

Patient Protection and Affordable Care Act (Public Law 111-148); 111th Congress; Mar. 23, 2010 124 STAT. 119; 906 pages.

"30-day unplanned readmission and death measures", http://www.medicare.gov/hospitalcompare/data/30-day-measures.html; downloaded on Nov. 3, 2014; 2 pages.

"Thinking Outside the Pillbox: A System-wide Approach to Improving Patient Medication Adherence for Chronic Disease"; located at http://www.nehi.net/publications/17-thinking-outside-the-pillbox-a-system-wide-approach-to-improving-patient-medication-adherence-for-chronic-disease/view; Aug. 12, 2009; pp. 1-21; New England Healthcare Institute.

"PIMCO Variable Insurance Trust"; Global Bond Portfolio; Semiannual Report; Jun. 30, 2012; pp. 1-42; PIMCO.

"SNL Financial Introduces Complete Group and Insurance Industry Data"; located at http://www.prweb.com/releases/2008/04/prweb906344.htm; Apr. 30, 2008; pp. 1-3; Vocus PRW Holdings, LLC.

Pitts et al.; "United States: Hospital Readmissions Reduction Program May Impact Post-Acute Providers"; located at http://www.mondaq.com/unitedstates/x/183022/Healthcare/Hospital+ Readmissions+Reduction+Program+May+Impact+PostAcute+ Providers; Jun. 21, 2012; pp. 1-10; Mondaq.

* cited by examiner

MANAGING A RISK OF A LIABILITY THAT IS INCURRED IF A SUBJECT TREATED FOR A CONDITION IS RETREATED WITHIN A SPECIFIED TIME PERIOD

If an Application Data Sheet (ADS) has been filed on the filing date of this application, it is incorporated by reference herein. Any applications claimed on the ADS for priority under 35 U.S.C. § § 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority application(s)). In addition, the present application is related to the "Related applications," if any, listed below.

RELATED APPLICATIONS

U.S. patent application Ser. No. 13/956,146, titled MANAGING A RISK OF A LIABILITY THAT IS INCURRED IF ONE OR MORE SUBJECTS EACH TREATED FOR A RESPECTIVE CONDITION ARE RETREATED WITHIN A RESPECTIVE SPECIFIED TIME PERIOD, naming Grace Hsu Huynh, Roderick A. Hyde, Eric C. Leuthardt, Tony S. Pan, Lowell L. Wood, Jr., as inventors, filed on 31 Jul. 2013, is related to the present application.

U.S. patent application Ser. No. 13/956,157, titled GENERATING A DESCRIPTION OF, AND AN OFFER TO TRANSFER OR A SOLICITATION OF AN OFFER TO ACQUIRE, AN ASSET THAT INCLUDES AT LEAST ONE RETREATMENT CONTRACT, naming Grace Hsu Huynh, Roderick A. Hyde, Eric C. Leuthardt, Tony S. Pan, Lowell L. Wood, Jr., as inventors, filed on 31 Jul. 2013, is related to the present application.

If the listings of applications provided above are inconsistent with the listings provided via an ADS, it is the intent of the Applicant to claim priority to each application that appears in the Priority applications section of the ADS and to each application that appears in the Priority applications section of this application.

All subject matter of the Priority applications and the Related applications and of any and all parent, grandparent, great-grandparent, etc. applications of the Priority applications and the Related applications, including any priority claims, is incorporated herein by reference to the extent such subject matter is not inconsistent herewith.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

An embodiment includes determining a risk that a subject treated for a condition will be retreated within a time period, and calculating, in response to a determined risk, a fee for taking an action if the subject is retreated within the time period.

Another embodiment includes determining a risk that a subject treated for a condition will be retreated for the condition within a time period, and calculating, in response to a determined risk, a fee for taking an action if the subject is retreated for the condition within the time period. The term "retreated for the condition" can, for example, encompass retreatment for a complication arising from the condition or from the treatment of the condition.

Such embodiments may aid in managing a risk of a liability that may be incurred if a subject treated for a condition is retreated for the condition, for a complication arising from the condition or from the treatment of the condition, or for another reason, within a specified retreatment time period.

Examples of such liability include monetary or other penalties, a requirement that the treating party pay some or all of the costs of the subject's retreatment, and a reduction in insurance reimbursements for the subject or other subjects during a penalty time period that commences in response to the subject being retreated within the retreatment time period.

Furthermore, examples of a subject being treated and then retreated for a condition include a subject who undergoes heart-bypass surgery (treatment), is released from the hospital, but then is readmitted to the hospital a few days later for complications arising from the surgery (retreatment), and a subject who complains of thoracic pain, undergoes an appendectomy to relieve the pain (treatment), but then has his gall bladder, which is later discovered to be the true source of his pain, removed a week later (retreatment). In the former example, the liability for retreatment may arise under the theory that had the surgeon competently performed the heart bypass, neither the complications, nor the costs associated with retreating the subject for the complications, would have arisen; and in the latter example, the liability for retreatment may arise under the theory that had the treating physician properly diagnosed the cause of the subject's pain initially, neither the need for the appendectomy, nor the costs associated with the appendectomy, would have arisen.

Moreover, examples of a subject being treated for a condition and then retreated for something other than the condition within a specified time period include a subject who undergoes heart-bypass surgery (treatment), is released from the hospital, but then is struck by a car and readmitted to the hospital a few days later for a broken arm.

In addition, examples of the fee include an insurance premium, and examples of the action include partially or fully reimbursing, e.g., the treatment provider, for any penalties or other costs incurred due to the retreatment of the subject.

Furthermore, one or more steps of such embodiments can be performed by a computing apparatus.

DETAILED DESCRIPTION

Figure 1:
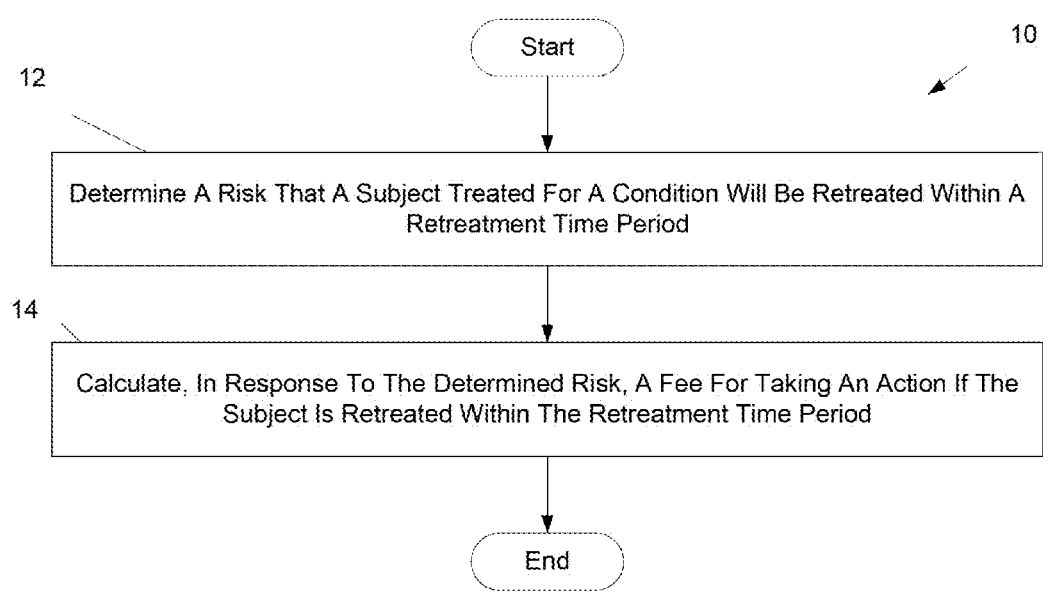
FIG. 1 is a flow diagram of a method for managing a risk that a subject treated for a condition will be retreated for the condition, or for some other reason, within a retreatment time period, according to an embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

One or more embodiments are described with reference to the drawings, wherein like reference numerals may be used to refer to like elements throughout. In the following description, for purposes of explanation, numerous specific details are set forth in order to provide a thorough understanding of the one or more embodiments. It may be evident, however, that one or more embodiments may be practiced without these specific details. In other instances, well-known structures and devices are shown in block-diagram form in order to facilitate describing one or more embodiments.

The Patient Protection and Affordable Care Act (Public Law 111-148), which is commonly (and hereinafter) referred to as "Obamacare," was signed into law by President Barack Obama on Mar. 23, 2010, and is administered by the Secretary of Health and Human Services acting through the Health Resources and Services Administration.

Section 3025 of Obamacare, titled Hospital Readmissions Reduction Program, provides for a financial penalty to any Medicare reimbursed hospital that has, during the course of a year, a greater-than-average number of patient readmissions within thirty days of the patients' respective discharge dates. And although the efficacy of the readmission penalty in reducing healthcare costs, particularly without jeopardizing patients' health, has been widely debated, it is speculated that Congress may someday broaden the readmission penalty to include, e.g., treated conditions other than those currently specified, funds other than Medicare reimbursements, retreatments that do not include a hospital readmission, and healthcare-treatment providers (e.g., physicians, medical clinics, urgent-care clinics, non-physician treatment providers) other than hospitals.

Therefore, it is speculated that private health insurance companies may someday include in their contracts with hospitals, physicians, and other treatment providers penalties for patient readmission or for other patient retreatment within a certain time period, e.g., thirty days. For example, some contracts may include retreatment penalties for treating a previously treated condition, other contracts may expand the definition of retreatment to include treating complications arising from the previously treated condition or the treatment thereof, while still other contracts may expand the definition of retreatment to include treating a condition that is unrelated to the previously treated condition.

Consequently, a healthcare-treatment provider may want to manage its risk of incurring a liability if a subject whom the provider treated for a condition is retreated for the condition, or for another reason (e.g., for another condition), within a time period specified, e.g., by the government or a medical insurer. For example, a healthcare-treatment provider may want to purchase insurance that will partially or fully reimburse the provider for any monetary costs that the provider incurs due to a treated subject's retreatment within the specified time period.

Described below are embodiments of that one can use to assist a healthcare-treatment provider in managing its risk of incurring such a liability. By using an embodiment described herein, a hospital could manage its risk of incurring a financial penalty if a patient whose hip a doctor at the hospital replaced is readmitted to the hospital, or to another hospital, for an infection around the hip within thirty days from the day on which the hospital discharged the patient for the hip-replacement surgery. Or, an insurer may use an embodiment described herein to assist a hospital in managing its risk of incurring a financial penalty if an excessive number of patients treated at the hospital for various conditions during a coverage period are readmitted to the hospital, or to another hospital, for complications arising from the treated conditions within a respective thirty days from each of the patients' respective discharge date.

Furthermore, an embodiment described herein may be utilized by parties other than healthcare providers.

Extensive statistical data on actual patient hospital readmissions, and extensive statistical analysis of potential patient hospital readmissions based on a variety of variables, are publicly available. For example, the federal government provides myriad data on hospital readmissions, see for example, the website: http://hcupnet.ahrq.gov/HCUPnet.jsp?Id=485C9DBC4B9A2A67&Form=MAIN SEL&JS=Y&Action=%3E%3ENext%3E%3E&_MAIN SEL=Readmission%20Summary%20Tables; and www.medicare.gov. Multiple variables affecting readmission include, but are not limited to, disease or condition treated, demographics, anthropometric and clinical values, functional status, nutritional histories, medical histories, etc. See, for example, *Am J Clin Nutr* June 1997 vol. 65 no. 6 1714-1720, which is incorporated herein by reference.

Additionally, numerous studies have been conducted and are publicly available for the skilled artisan to use the data to determine a risk factor for readmission or other retreatment of a specific individual. Without limitation, and for example, in the study titled *"Diagnoses and Timing of 30-Day Readmissions After Hospitalization for Heart Failure, Acute Myocardial Infarction, or Pneumonia,"* (JAMA. 2013; 309(4):355-363. doi:10.1001/jama.2012.216476, and incorporated herein by reference) researchers studied 2007 to 2009 Medicare fee-for-service claims data for 30-day readmissions after hospitalization for heart failure, acute myocardial infarction, and pneumonia. They found that the 30-day readmission rate after heart failure hospitalization was 24.8 percent. Further, the 30-day readmission rate after acute myocardial infarction hospitalization was 19.9 percent. In addition, the 30-day readmission rate after pneumonia hospitalization was 18.3 percent. Further, the average age of readmissions was 80.3 years for patients originally hospitalized for heart failure, 79.8 years for patients originally hospitalized for acute myocardial infarction, and 80 years for patients originally hospitalized for pneumonia. They also found that the majority of all readmissions occurred within 15 days of hospitalization: Sixty-one percent of heart failure readmissions, 67.6 percent of acute myocardial infarction readmissions, and 62.6 percent of pneumonia readmissions occurred in this time period. Among all readmissions, approximately one-third occurred from day 16 through day 30 post-hospitalization. In addition, the median time period between hospitalization and readmission was 12 days for heart failure patients, 10 days for acute myocardial infarction patients and 12 days for pneumonia patients. Of readmissions after a heart-failure hospitalization, 87.5 percent were readmitted once, 9.7 percent were readmitted twice, and 2.8 percent were readmitted three or more times. Of readmissions after an acute-myocardial-infarction hospitalization, 97.4 percent were readmitted once, 2.4 percent were readmitted twice, and 0.2 percent were readmitted three or more times. Of readmissions after a pneumonia hospitalization, 95.1 percent were readmitted once, 4.3 percent were readmitted twice, and 0.6 percent were readmitted three or more times. Of readmissions after a heart-failure hospitalization, the most common diagnosis was heart failure at 35.2 percent. Of readmissions after an acute-myocardial-infarction hospitalization, the most common diagnosis was heart failure at 19.3 percent. Of readmissions after a pneumonia hospitalization, the most common diagnosis was recurrent pneumonia at 22.4 percent. Cardiovascular disease was the cause of 52.8 percent of readmissions after heart-failure hospitalization and 53.4 percent of readmissions after acute-myocardial-infarction hospitalization. Respiratory disease accounted for 38.5 percent of readmissions after pneumonia hospitalization. The five most common readmission diagnoses accounted for 55.9 percent for heart-failure readmissions, 44.3 percent of acute-myocardial-infarction readmissions and 49.6 percent of pneumonia readmissions.

In the study titled *"Pediatric Readmission Prevalence and Variability Across Hospitals,"* (JAMA. 2013 Jan. 23; 309(4): 372-80. doi: 10.1001/jama.2012.188351, incorporated herein by reference) researchers studied 568,845 admissions at 72 children's hospitals between Jul. 1, 2009 and Jun. 30, 2010. The authors categorized hospitals as having high readmission rates if the rates were one standard deviation above the mean, and low readmission rates if they were one standard deviation below the mean. The researchers found that the 30-day unadjusted readmission rate for all hospitalized children was 6.5 percent. Further, the adjusted 30-day readmission rate for hospitals with high readmission rates were 7.2 percent compared with 5.6 percent for low-readmission hospitals—a difference of 28.6 percent. Further, the adjusted 30-day readmission rates for the 10 admission diagnoses with the highest readmission prevalence were 17 percent to 66 percent greater in hospitals with high readmission rates compared with hospitals with low readmission rates. In addition, the 30-day readmission rate for sickle cell, one of the 10 diagnoses with the highest rate of readmissions, was 20.1 percent in hospitals with high readmission rates and 12.7 percent in hospitals with low readmission rates.

Additional statistical information regarding the number of stays, the mean cost per stay, the readmission rate, and the mean cost of readmission for a number of treatments for respective conditions can be found at, or via the following website: http://hcupnet.ahrq.gov/HCUPnet.jsp?Id=485C9DBC4B9A2A67&Form=MAINSEL&JS=Y& Action=%3E%3ENext%3E%3E&_MAINSEL=Read mission%20Summary%20Tables. For example, in the U.S. during 2011, there were 297,169 appendectomies performed at a mean cost of US$11,985 for each appendectomy. Out of these appendectomy patients, 17,894 (6.05%) were readmitted within 30 days—a readmission for any reason is counted as a readmission in this data—and the mean cost for each readmission was US$11,106.

And similar information can be found at, or via, the following website: http://www.medicare.gov/hospitalcompare/data/rcd/30-day-measures.aspx?AspxAutoDetect-CookieSupport=1.

FIG. 1 is a flow diagram 10 of a method for managing a risk that a subject treated for a condition will be retreated within a retreatment time period, according to an embodiment.

Figure 15:
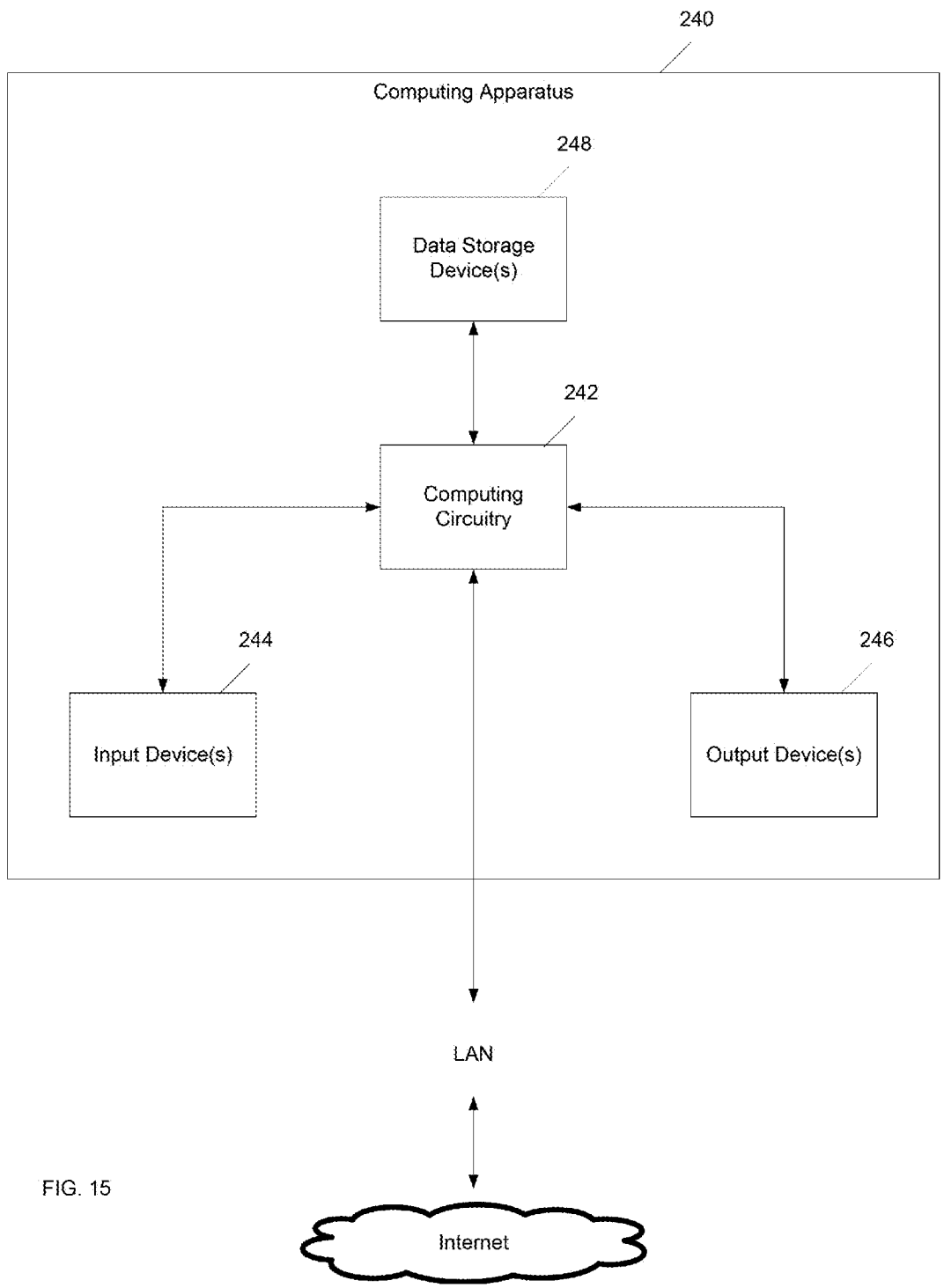
FIG. 15 is a block diagram of a computing apparatus that can perform one or more steps of each of the methods described above in conjunction with FIGS. 1-2, 4-7, 9-11, and 14, according to an embodiment.

Referring to a step 12, a computing apparatus automatically determines a risk that a subject treated for a condition will be retreated within a retreatment time period, and referring to a step 14, the computing apparatus automatically calculates, in response to the determined risk, a fee for taking an action if the subject is retreated for the condition, or for another reason, within the retreatment time period—an embodiment of a computing apparatus configured to perform the steps 12 and 14, and the steps of other methods described hereinafter, is described below in conjunction with FIG. 15. For example, a computing apparatus may determine a risk that a subject who undergoes an angioplasty in one artery will require further angioplasty in that artery, or will undergo angioplasty in another artery, within thirty days from the first angioplasty procedure, and may calculate, in response to the determined risk, an insurance premium for an insurer to pay a penalty, or to pay some or all of the cost of the subsequent angioplasty(ies), if the subject undergoes at least one other angioplasty within thirty days from the first angioplasty.

Referring again to the step 12, the computing apparatus may determine the risk by mathematically determining, using statistics or other mathematical techniques, a probability that the subject will be retreated within the retreatment time period. For example, the computing apparatus may determine the probability that a subject who was admitted to a facility for treatment of a condition will be readmitted to the same facility, or to a different facility, within the retreatment time period for retreatment of the condition or for another reason (e.g., an illness unrelated to the condition for which the subject was previously treated).

Furthermore, the computing apparatus may determine the risk before the subject is even treated for the condition, at some point during a period of time over which the subject is being treated for the condition, or after the subject has completed treatment for the condition (but before the expiration of the retreatment time period). And the computing apparatus may subsequently re-determine and refine the determined risk one or more times before the expiration of the retreatment time period.

Moreover, the subject may be a patient of the treatment provider, or may have a non-patient relationship to the treatment provider; an example of the latter is where the subject is a participant in a clinical trial. And although an embodiment of the method described in conjunction with FIG. 1 contemplates a human subject, the concepts described in this disclosure may also apply to a non-human subject such as a pet or a racehorse.

In addition, examples of treatments that the subject may receive for the condition include any type of surgery, chemotherapy and other drug therapies, hormone therapy, physical therapy, organ transplantation, blood transfusion, joint and other body-part replacement, dental procedure, psychological therapy or counseling, psychiatric therapy or counseling, sleep therapy, chiropractic therapy, massage therapy, shock therapy, homeopathic therapy, and acupuncture.

Furthermore, examples of conditions for which the subject may be treated and retreated include medical conditions, physical conditions, mental conditions, addictions, injuries, and illnesses.

Moreover, the terms "retreat," "retreating," "retreated," and "retreatment" encompass retreating the subject for the same condition for which he/she was previously treated, or retreating the subject for another reason. For example, retreating the subject includes treating the subject with the same treatment with which the subject previously was treated, treating the subject with a treatment different from the treatment with which the subject previously was treated, treating the subject for a complication arising from the previously treated condition or from the previous treatment itself, readmitting the subject to a facility where the subject previously was treated, readmitting the subject to a facility other than the facility where the subject previously was treated, a provider counseling or otherwise seeing a subject who seeks retreatment even if the provider determines that further retreatment is not needed, and even treating the subject for another condition or reason that is independent of the condition for which the subject previously was treated. An example of the latter is the subject having had a hip replaced, and then being admitted to a hospital for appendicitis within thirty days of discharge from the hip replacement.

In addition, the retreatment time period may be any suitable time period such as thirty days, and may begin at any time, for example, as soon as, or after, the subject completes treatment for the condition, or as soon as, or after, the subject is discharged from a hospital or other treatment provider that treated the subject for the condition.

And referring again to the step 14 of FIG. 1, the computing apparatus may calculate the fee by mathematically calculating, using statistics or other mathematical techniques, the fee in response to the risk determined at the step 12. For example, the computing apparatus may calculate the fee at any time after the risk is determined at the step 12, and the computing apparatus may subsequently recalculate and refine the fee one or more times before the expiration of the retreatment time period.

Furthermore, the fee may include an insurance premium or other monetary payment, or may include a non-monetary payment (e.g., a security) or a non-monetary obligation (e.g., an agreement to perform a service, or the performance of a service).

Moreover, examples of taking the action include paying money to a beneficiary of a retreatment contract (an embodiment of a retreatment contract is described below in conjunction with FIG. 3) such as a retreatment insurance policy, partially or fully reimbursing the beneficiary for the cost of retreating the subject or for a penalty associated with retreating the subject, paying the partial or full cost of the retreating directly to a retreatment provider, or surrendering an item or service of value to a beneficiary or to an appropriate public or private agency. Alternatively, taking the action may include retreating the subject if, before the subject is retreated, it is determined that the subject requires retreatment, or that the subject should be retreated, within the retreatment time period. For example, if the retreatment is minor (e.g., a doctor's office visit), then the action may be providing the retreatment; but if the retreatment is major (e.g., surgery), then the action may paying for the retreatment by a more qualified provider. Furthermore, taking the action may encompass taking more than one action either together or separately.

Still referring to FIG. 1, alternate embodiments of the method represented by the flow diagram 10 are contemplated. For example, the method may include steps in addition to the steps 12 and 14, may include only a single one of the steps 12 and 14, or one or both of the steps 12 and 14 may be modified. Furthermore, the computing apparatus may perform one or both of the steps 12 and 14 in a non-automatic manner, or in response to human or other intervention; alternatively, another type of apparatus, or even a human, may perform one or both of these steps.

Figure 2:
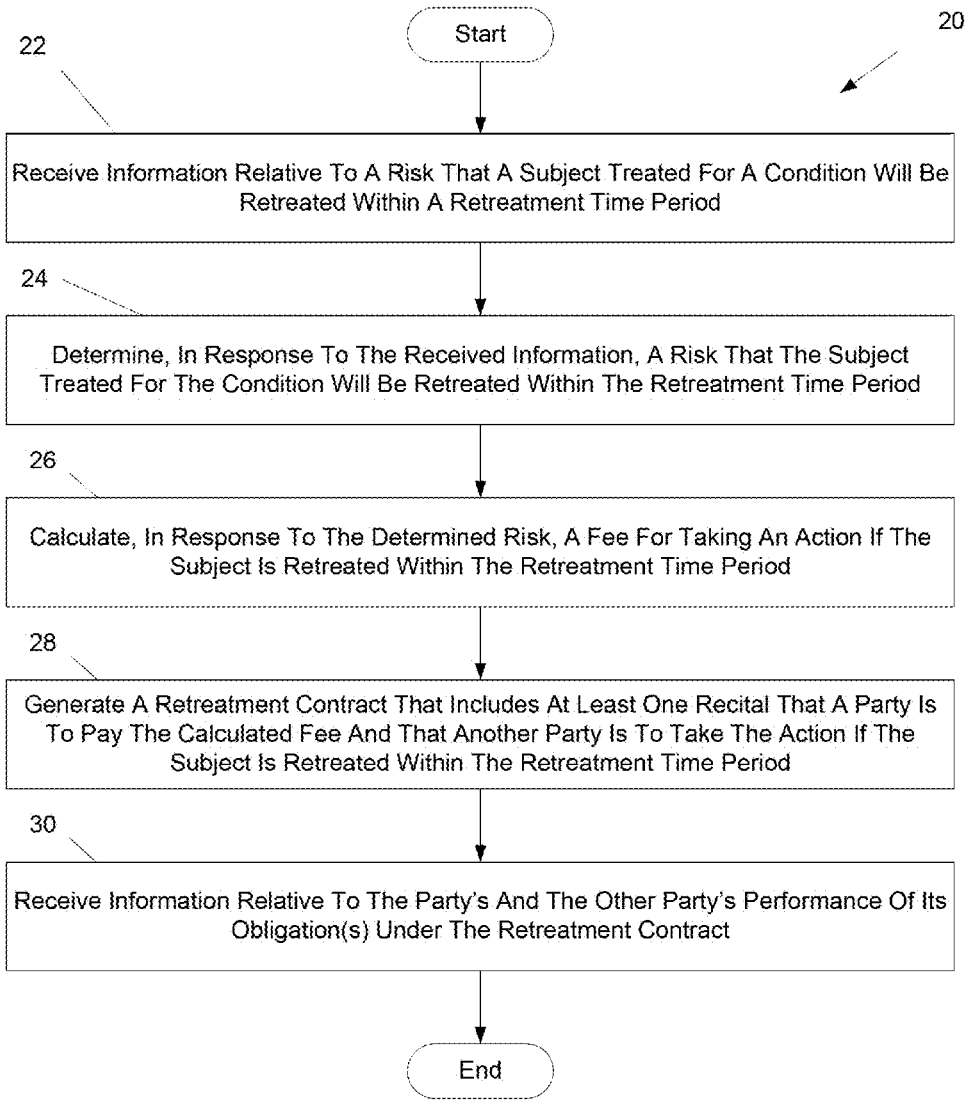
FIG. 2 is a flow diagram of a method for managing a risk that a subject treated for a condition will be retreated for the condition, or for some other reason, within a retreatment time period, according to another embodiment.

FIG. 2 is a flow diagram 20 of a method for managing a risk that a subject treated for a condition will be retreated within a retreatment time period, according to another embodiment.

Referring to a step 22, a computing apparatus automatically receives information relative to a risk that a subject treated for a condition will be retreated for the condition, or for another reason (e.g., another condition), within a retreatment time period. Examples of such information include information about the subject, such as the time of year during which the subject is/was treated for the condition, the geographical location(s) of the subject during and after treatment, the current health, health history, and health profile of the subject, how many times the subject has been treated previously for the condition, and other conditions, if any, for which the subject has been treated or is expected to receive treatment. Other examples of such information include information about the treatment, such as the type, length, success rate, and other characteristics of the treatment, information about the treatment provider (e.g., a physician, a hospital), such as the success rates of the treatment provider in treating the condition, and information about any post-treatment regimen and how closely the subject followed/is expected to follow this regimen. Still other examples of such information include information about the condition, such as the type, severity, cure rate, and other characteristics of the condition, about the scope of "retreated" (e.g., does "retreated" encompass only retreatment for the previously treated condition, or does it encompass treatment for one or more other reasons), and about the starting time and length of the retreatment time period.

Then, referring to a step 24, which can be similar to the step 12 of FIG. 1, the computing apparatus automatically determines, in response to the information received at the step 22, a risk that the subject treated for the condition will be retreated within the retreatment time period.

Next, referring to a step 26, which can be similar to the step 14 of FIG. 1, the computing apparatus automatically calculates, in response to the risk determined at the step 24, a fee for taking an action if the subject is retreated within the retreatment time period.

Then, referring to a step 28, the computing apparatus automatically generates a retreatment contract that includes at least one recital that a party is to pay the calculated fee, and that another party is to take an action if the subject is retreated within the retreatment time period.

Still referring to the step 28, the computing apparatus may generate the retreatment contract in any suitable format, such as in electronic format or on paper via a printer that forms part of, or that is coupled to, the computing apparatus.

The retreatment contract can be any type of contract, such as a risk-transfer financial instrument, financial-swap agreement, insurance policy, or any other legally enforceable instrument, that includes at least one recital that the party is to pay the calculated fee and that another party is to take the action if the subject is retreated within the retreatment time period. An embodiment of the retreatment contract is further described below in conjunction with FIG. 3.

The party that is obligated to pay the fee can be a single person, multiple persons, or any one or more non-person entities such as a business or trust. Examples of the fee-paying party include a buyer of a right under the retreatment contract, and a beneficiary under the retreatment contract. Examples of such a beneficiary include the subject, a provider (e.g., a physician, hospital, medical clinic, or medical association) associated with treating the subject for the condition, and the subject's medical insurer under an insurance policy that is separate from the retreatment contract. The party that is obligated to pay the fee may also be referred to as a buyer or purchaser of the retreatment contract.

The other party that is obligated to take the action if the subject is retreated within the retreatment period also can be a single person, multiple persons, or any one or more non-person entities such as a business or trust. Examples of the obligated-to-take-the-action party include an insurer (e.g., of the treatment provider) under the retreatment contract, the subject, and a treatment provider (e.g., a physician, hospital, medical clinic, or medical association) associated with treating or retreating the subject for the condition. In the case of the subject being the party obligated to take the action, the subject may be confident enough in his/her ability to prevent the need for retreatment by, for example, complying with a post-treatment regiment, that he/she may sell the retreatment contract to, and thus act as an insurer of, the treatment provider. And in the case of the treatment provider being the party obligated to take the action, the provider may be confident in its ability to prevent the need for the subject's retreatment, and, therefore, may sell the contract to, and thus act as an insurer of, the subject. The other party that is obligated to take the action may also be referred to as a seller or of the retreatment contract.

Still referring to the step 28, examples of taking the action, retreatment of the subject, and the retreatment time period are described above in conjunction with the step 14 of FIG. 1.

Next, referring to a step 30, the computing apparatus automatically receives information relative to the fee-paying party's and the obligated-to-take-the-action party's performances of their obligations under the retreatment contract. For example, the computing apparatus may receive such information in any suitable manner, such as from the internet via a local area network (LAN). Moreover, the computing apparatus may track the fee-paying party's payment of the fee calculated at the step 26, and may notify the obligated-to-take-the-action party if the fee-paying party is late with a payment. The computing apparatus also may receive information indicating that the subject has been retreated within the retreatment period, and, in response to this information, may generate a notice to the obligated-to-take-the-action party that it needs to take the action specified in the retreatment contract. The computing apparatus may also track the obligated-to-take-the-action party, and may notify the fee-paying party or an enforcement agency (e.g., a government agency) if the obligated-to-take-the-action party does not timely take the action that it is obligated take under the retreatment contract.

Still referring to FIG. 2, alternate embodiments of the method represented by the flow diagram 20 are contemplated. For example, the method may include steps in addition to the steps 22-30, may omit one or more of the steps 22-30, or one or more of these steps may be modified. Furthermore, the computing apparatus may perform one or more of the steps 22-30 other than automatically, or in response to human or other intervention; or another type of apparatus, or even a human being, may perform one or more of these steps. Moreover, the computing apparatus may automatically generate more than one retreatment contract relating to the retreatment of the subject.

Figure 3:
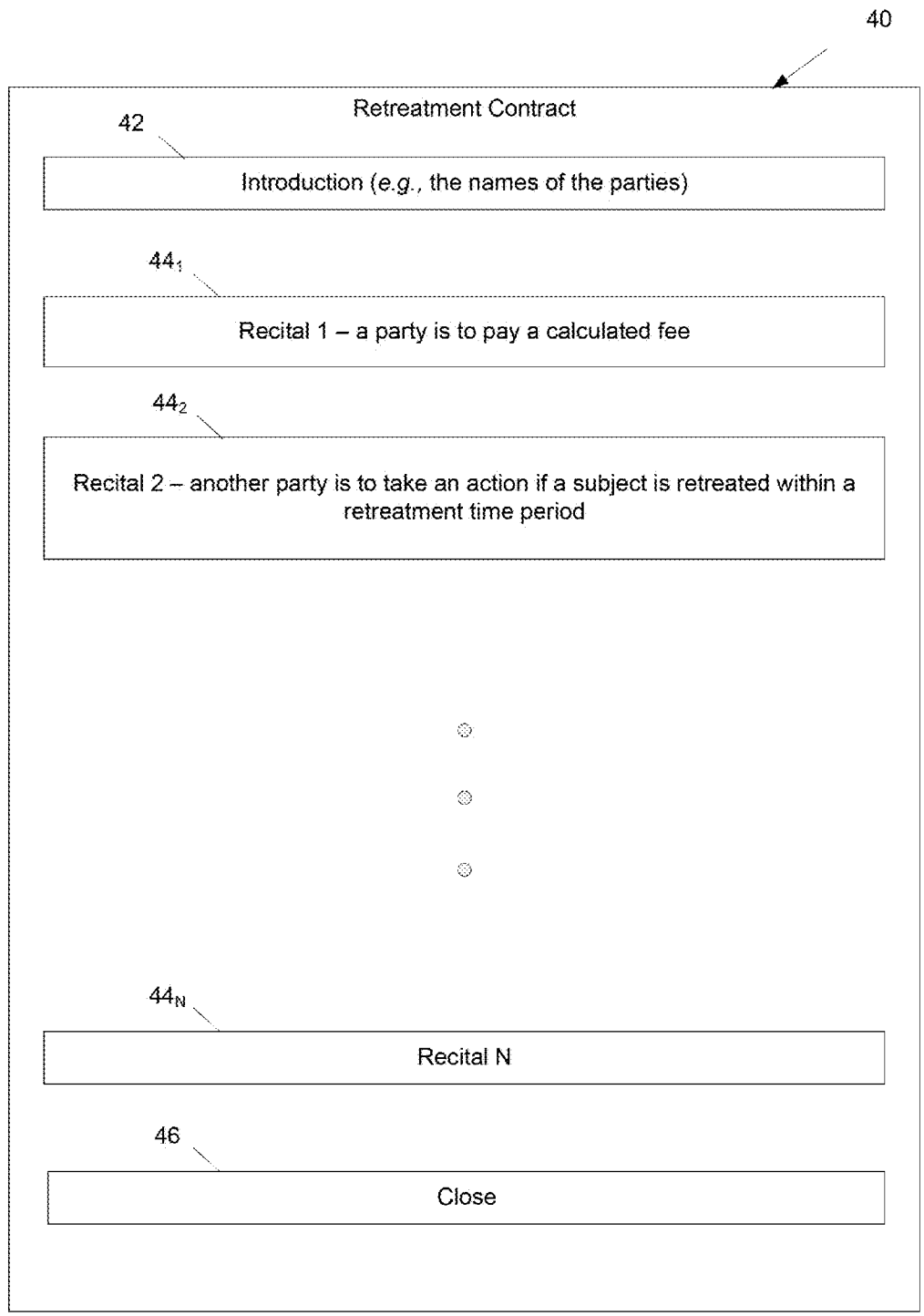
FIG. 3 is a diagram of a retreatment contract, according to an embodiment.

FIG. 3 is a diagram of a retreatment contract 40, which a computing apparatus may automatically generate at the step 28 of FIG. 2, according to an embodiment.

The retreatment contract 40 includes an introduction 42, N recitals $44_1$-$44_N$, where N≥1, and a closing 46, and may be fixed in any suitable non-transitory format such as paper or electronic.

The introduction 42 of the retreatment contract 40 may include, for example, the names and addresses of the parties to the contract, the names and addresses of any beneficiaries under the contract, the name and address of the subject, and a glossary or definitions of words or phrases that appear in the contract.

The recitals 44 each include a respective one or more terms of the retreatment contract 40; a recital can be in the form of a clause, paragraph, article, section, or other portion of the retreatment contract, and can be written expressly in the retreatment contract or incorporated into the retreatment contract by reference to another document (e.g., an appendix or another instrument) in which the recital is written.

Furthermore, the recitals 44 can specify the obligations of the parties to the retreatment contract 40, the conditions in response to which the obligations arise, the rights of any beneficiaries, and standard contract "boiler-plate" such as actions that constitute a breach of the contract, the venue for any dispute that may arise under the contract, the jurisdiction under whose laws the contract is to be interpreted, the effective start date of the contract, and the date (if any) on which the contract ends.

For example, Recital 1 $44_1$ of the contract 40 may recite, per the step 26 of the flow diagram 20 of FIG. 2, that a party to the contract is to pay a calculated fee, and Recital 2 $44_2$ may recite, per the step 28 of the flow diagram 20, that another party to the contract is to take an action if the subject is retreated within the retreatment time period.

Recital 1, Recital 2, or one or more other recitals of the retreatment contract 40 can include all of the other terms of the contract.

Examples of such other terms include the amount of the fee, the schedule for payment of the fee, the action that a party is required to take if the subject is retreated within the retreatment period and the time period for taking the action, a description of the condition and the treatment, the length and start date of the retreatment period, and the obligations of non-parties. Regarding the action that a party is required to take if the subject is retreated within the retreatment time period, a recital of the retreatment contract 40 may specify, for example, that such action is a payout of an amount of money to, e.g., the subject or to a retreatment provider. For example, the recital may specify a fixed amount of money, a fixed percentage of the retreatment cost, an algorithmic payout (e.g., a fixed amount, plus a percentage of the retreatment costs above the fixed amount) or a cap on the payout. And regarding obligations of non-parties, the retreatment contract 40 may specify, for example, that the subject must adhere to a specified post-treatment regimen or be monitored post treatment by a specified entity (e.g., follow-up visits to the treatment provider) as a condition precedent for a party to take a specified action if the subject is retreated within the retreatment time period.

Still other examples of such other terms include limitations on the retreatment, limitations on a size of a portion of a party's obligations or rights under the contract that the party can transfer to a third party and the timing of such a transfer, and that a party be bonded or insured.

Yet another example of such other terms includes that the party paying the fee also pay an additional fee, or surrender an item or service of value, if the subject is retreated within the retreatment time period and the cost of taking the action exceeds a specified threshold. For example, if the party paying the fee is also the party that treated the subject, then such a penalty term can provide an incentive for the party to treat the subject competently, and to diligently follow up with the subject post treatment, instead of providing subpar treatment and follow-up care and relying on the other party to cover the costs of retreatment.

Still referring to FIG. 3, the close 46 of the contract 40 may include the names, titles, and signatures of the parties, or of respective persons authorized to sign the contract on behalf of the parties.

Alternate embodiments of the retreatment contract 40 are contemplated. For example, the introduction 42, the close 46, or both the introduction and close may be omitted from the contract, and any information that would otherwise be in the omitted one(s) of these sections instead may be included in one or more of the recitals 44. Furthermore, as described above in conjunction with FIG. 2, the retreatment contract 40 may be, or may include, an insurance policy or any other type of risk-transfer contract or risk-transfer financial instrument.

Referring to FIGS. 1-3, a computing apparatus automatically generating multiple retreatment contracts 40 is also contemplated. For example, to hedge its risk, a seller of one retreatment contract 40 may be a buyer of another retreatment contract 40, where both contracts cover retreatment of the same subject treated for the same condition.

Furthermore, after the retreatment contract 40 is generated and entered into by at least a fee-paying party (e.g., a buyer) and an obligated-to-take-an-action party (e.g., a seller) as described above in conjunction with FIGS. 2-3, then it is contemplated that any of the parties, and any beneficiaries, may transfer their respective rights and obligations under the contract to respective third parties. For example, the seller may transfer its right to collect the fee from the buyer, or its obligation to take the action if the subject is retreated, to a third party. Or, the seller may transfer its right to collect the fee from the buyer to a creditor as payment of debt that the seller owes the creditor. In addition, the seller may sell its right to collect the fee and its obligation to take the action; although the seller typically will make a reduced amount of money as compared to collecting the fee, it has shed the obligation to take the action. Likewise, the buyer, or a non-buyer beneficiary, entitled to receive the benefit of the taken action may transfer its right to receive this benefit to a third party.

Figure 4:
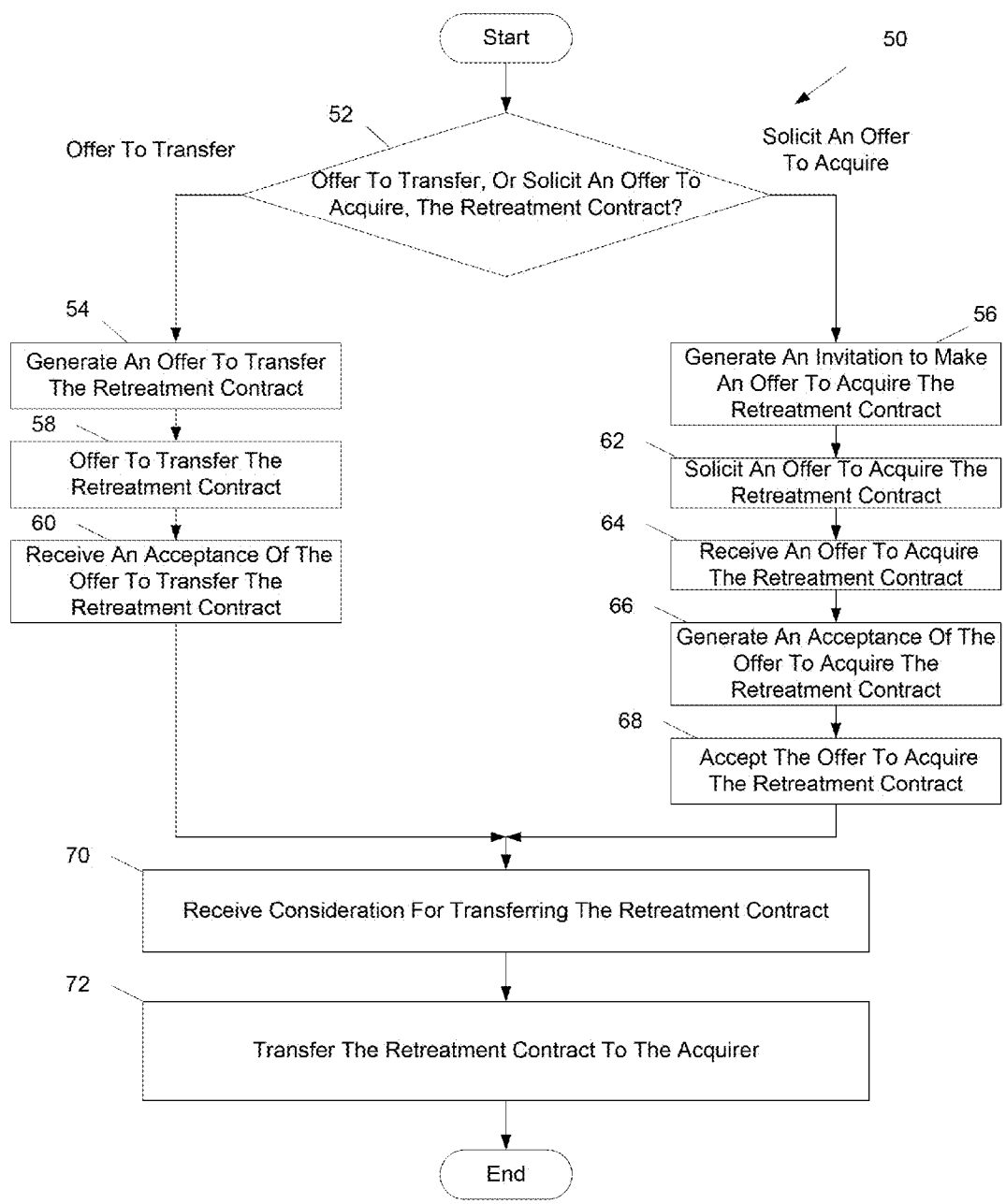
FIG. 4 is a flow diagram of a method for managing a transfer of a retreatment contract, according to an embodiment.

FIG. 4 is a flow diagram 50 of a method for transferring at least one right or obligation under a retreatment contract, such as the retreatment contract 40 of FIG. 3, according to an embodiment. Hereinafter, terms such as "transferring the retreatment contract" and "selling the retreatment contract" refer to the transfer/sale of one or more rights or obligations under the contract to one or more third parties, where the transfer may, or may not, be for money or other consideration in return. For example, referring to FIGS. 1 and 2, the beneficiary of the action to be taken by a party in the event that the subject is retreated within the retreatment time period may "transfer the retreatment contract" to a third party by transferring to the third party the right to receive the action taken if the action is taken. Or, a party entitled to receive the fee paid by another party under the retreatment contract may "sell the retreatment contract" to a third party by selling to the third party the right to receive the fee. Furthermore, although the flow diagram 50 describes an embodiment of the method in conjunction with the retreatment contract 40 of FIG. 3, it is understood that an embodiment of the method is suitable for retreatment contracts other than the retreatment contract 40, and for other contracts and instruments in general.

Referring to a step 52, a computing apparatus first determines automatically whether to offer the retreatment contract 40 (FIG. 3) for transfer or to solicit an offer to acquire the contract. The computing apparatus may make this determination based on information it receives regarding the transfer of the contract 40. For example, the computing apparatus may receive information indicating that a seller of the contract 40 would like to sell the contract to a third party for a specified price.

If the computing apparatus "decides" to offer the retreatment contract 40 for transfer, then the computing apparatus proceeds to a step 54; otherwise, the computing apparatus proceeds to a step 56.

Referring to the step 54, the computing apparatus automatically generates an offer to transfer the retreatment contract 40 (FIG. 3), where the generated offer may be in any suitable format such as paper or electronic format. For example, the computing apparatus may generate an offer to transfer to a third party the right to receive the fee (e.g., an insurance premium paid on a monthly basis) that a party is obligated to pay under the contract 40.

Next, referring to a step 58, the computing apparatus automatically makes an offer to transfer the retreatment contract 40 (FIG. 3). For example, the computing apparatus may cause the offer generated at the step 54 to be published in an online market place such as Craig's List® or E-Bay®, or may send the offer directly to potential transferees.

Then, referring to a step 60, the computing apparatus receives an acceptance of the offer to transfer the contract 40 (FIG. 3). For example, the computing apparatus may receive the acceptance from the accepting party in an email, text, voice communication, or other electronic communication received via the internet or a phone system.

But if, at the step 52, the computing apparatus instead "decides" to solicit an offer to acquire the contract 40 (FIG. 3) instead of offering to transfer the contract, then referring to the step 56, the computing apparatus automatically generates an invitation to make an offer to acquire the retreatment contract, where the generated invitation may be in any suitable format such as electronic or paper format. For example, the computing apparatus may generate an invitation to make an offer or bid to acquire the right under the contract 40 to receive the fee (e.g., an insurance premium paid on a monthly basis) due under the contract.

Next, referring to a step 62, the computing apparatus automatically solicits an offer to acquire the retreatment contract 40 (FIG. 3). For example, the computing apparatus may cause the invitation generated at the step 56 to be published in an online market place such as Craig's List® or E-Bay®, or may send the invitation directly to potential acquirers.

Then, referring to a step 64, the computing apparatus automatically receives an offer to acquire the contract 40 (FIG. 3). For example, the computing apparatus may receive the offer from the offering third party in an email, text, voice mail, or other electronic communication via the internet or a phone system.

Next, referring to a step 66, the computing apparatus automatically generates an acceptance of the received offer to acquire the retreatment contract 40 (FIG. 3), where the generated acceptance may be in any suitable format such as electronic or paper format.

Then, referring to a step 68, the computing apparatus automatically accepts the offer to acquire the retreatment contract 40 (FIG. 3). For example, the computing apparatus may send the acceptance generated at the step 66 via email to the third party who made the offer.

Next, after whichever of the step 60 and the step 68 that the computing apparatus performs, referring to a step 70, the computing apparatus automatically receives consideration from the acquirer for transferring the retreatment contract 40 (FIG. 3) to the acquirer. For example, the computing apparatus may receive an electronic payment from the credit card, debit card, or bank account of the acquirer. And if the acquirer is obligated to make one or more future payments (e.g., monthly insurance premiums), then the computing apparatus may also automatically receive or track these payments in due course.

Then, referring to a step 72, the computing apparatus automatically transfers the retreatment contract 40 (FIG. 3) to the acquirer. For example, the computing apparatus may generate and send to the acquirer a copy of the contract 40 and a purchase agreement that memorializes the details of the transfer.

Still referring to FIG. 4, alternate embodiments of the method represented by the flow diagram 50 are contemplated. For example, the method may include steps in addition to the steps 52-72, may omit one or more of the steps 52-72, or may modify one or more of these steps. Furthermore, the computing apparatus may perform one or more of the steps 52-72 other than automatically, or in response to human or other intervention; or another type of apparatus, or even a human, may perform one or more of these steps.

Referring to FIGS. 1-4, instead of managing its risk of incurring retreatment liability on a subject-by-subject basis (e.g., with a separate retreatment contract for each treated subject), a treatment provider, such as a hospital, may want to manage its risk of incurring retreatment liability over a period of time regardless of how many subjects are treated or retreated, or regardless of the conditions for which subjects are treated or retreated, during this period.

Figure 5:
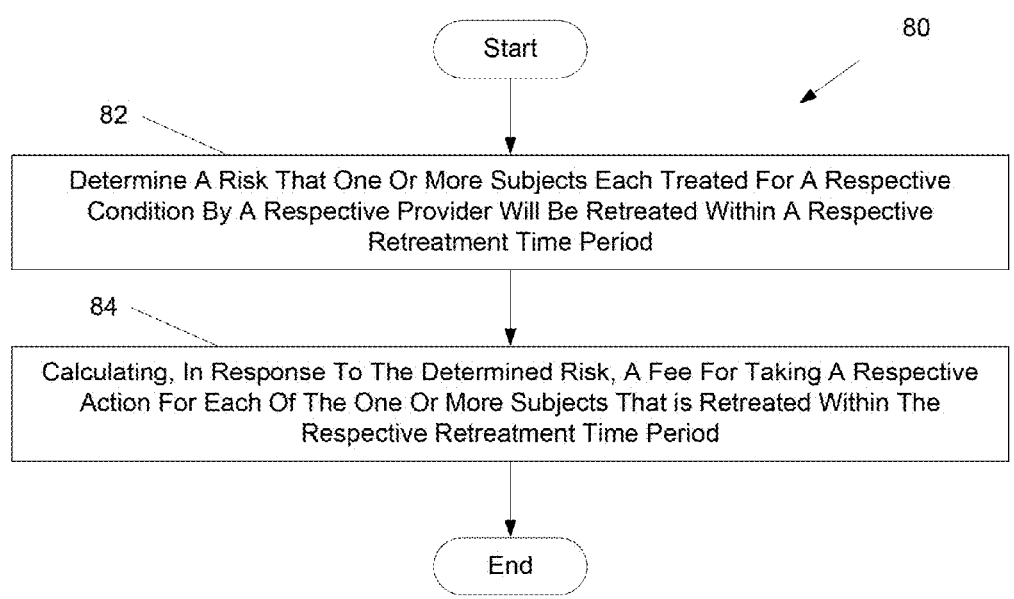
FIG. 5 is a flow diagram of a method for managing a risk that one or more subjects each treated for a respective condition will be retreated for the respective condition, or for a respective other reason, within a respective retreatment time period, according to an embodiment.
Figure 6:
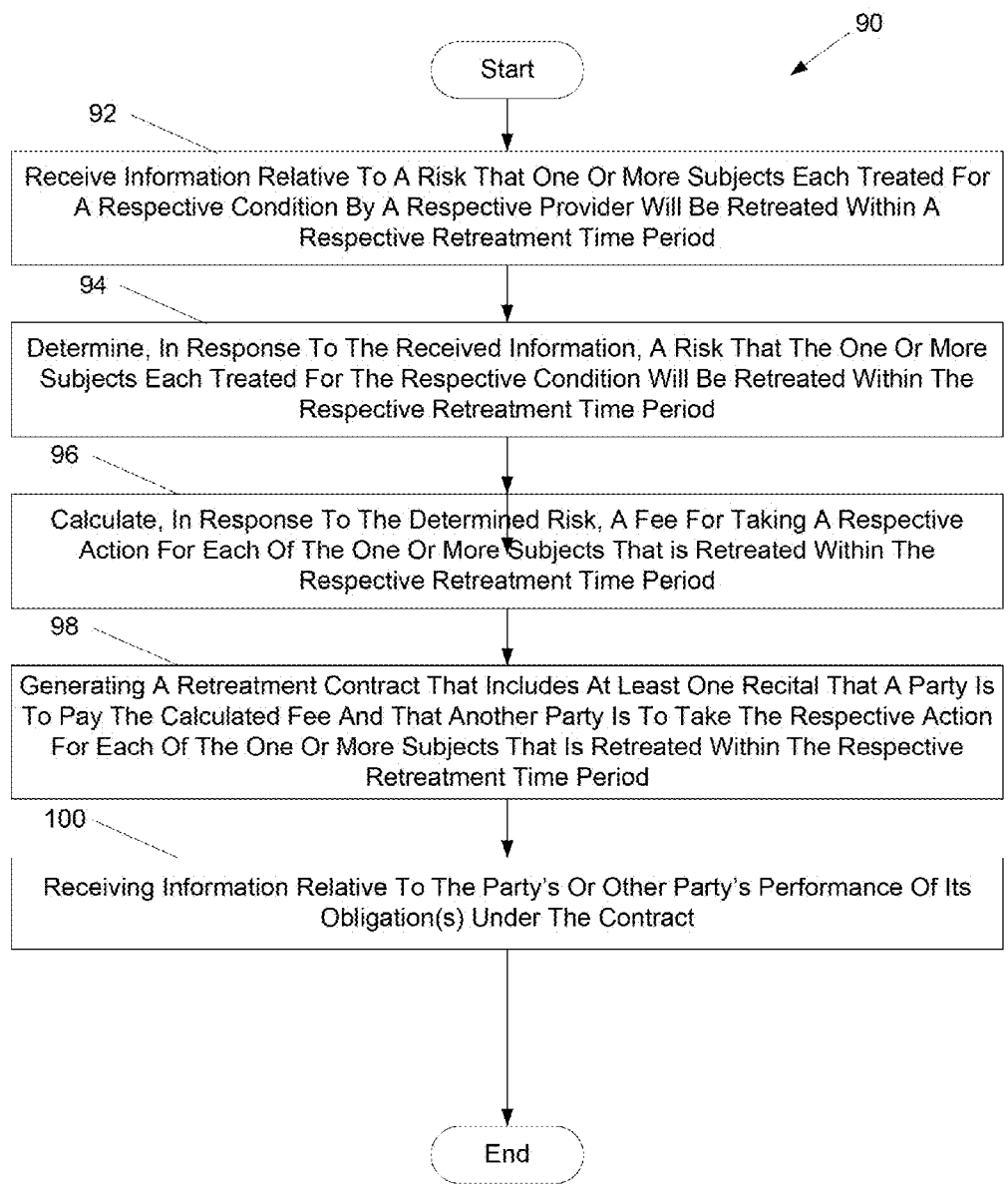
FIG. 6 is a flow diagram of a method for managing a risk that one or more subjects each treated for a respective condition will be retreated for the respective condition, or for a respective other reason, within a respective retreatment time period, according to another embodiment.

Consequently, described below in conjunction with FIGS. 5-6 are embodiments of methods that one can use to assist a treatment provider (e.g., a hospital) in managing its risk of incurring retreatment liability if one or more subjects treated by the provider for various conditions during a coverage period are retreated within respective retreatment time periods. Furthermore, embodiments of the below-described methods may be utilized by parties to the contract or third parties other than treatment providers.

FIG. 5 is a flow diagram 80 of a method for managing a risk that one or more subjects each treated for a respective condition by a respective treatment provider will be retreated within a respective retreatment time period, according to an embodiment.

Referring to a step 82, a computing apparatus automatically determines a risk that one or more subjects each treated for a respective condition by a respective provider will be retreated for the condition, or for another reason, within a respective retreatment time period, and referring to a step 84, the computing apparatus automatically calculates, in response to the determined risk, a fee for taking a respective action for each of the one or more subjects that is retreated within the respective retreatment time period.

Referring again to the step 82, the computing apparatus may determine the risk by mathematically determining, using statistics or other mathematical techniques, a probability that at least one of the one or more of the subjects will be retreated within the respective retreatment time periods. For example, the computing apparatus may determine the probability that at least one of the one or more subjects that were admitted to a facility for treatment of respective conditions will be readmitted to the same facility, or to a different facility, within the at least one respective retreatment time period associated with the at least one subject for retreatment of the respective condition or for another reason (e.g., an illness unrelated to the at least one respective condition for which the at least one of the one or more subjects was previously treated).

Furthermore, the computing apparatus may determine the risk for a coverage time period, which may be separate and distinct from the one or more retreatment time periods. In general, the coverage time period is a period (e.g., one year) during which each of the one or more subjects receives a least a portion of the respective treatment for the respective condition, or which overlaps with at least a portion of the respective retreatment time period for each of the one or more subjects. For example, for a hospital where doctors perform hip replacements, the coverage period may be a span during which each of the one or more subjects has hip-replacement surgery; that is, all of subjects who have hip-replacement surgery during the coverage period form the "one or more subjects" for which the computing apparatus calculates the risk. Alternative examples include the coverage period being a span during which each of the one or more subjects is at least admitted for hip-replacement surgery, a span during which each of the one or more subjects is discharged from hip-replacement surgery, and a span during which the respective retreatment period for each of the one or more subjects begins or ends. As an example of the latter, if the coverage period runs from Jan. 1, 2013 to Dec. 31, 2013 and a subject with whom is associated a thirty-day retreatment period is discharged Dec. 15, 2012, then the subject falls within the coverage period because his retreatment period ends in January 2013; in contrast, if the subject is discharged Dec. 15, 2013, then the subject does not fall within the coverage period because his retreatment period ends in January 2014, which is outside of the coverage period—the subject may fall within the coverage period of another retreatment contract, however.

Moreover, the computing apparatus may determine the risk before or during the coverage time period (but before the expiration of all of the retreatment time periods for the one or more subjects).

In addition, the computing apparatus may determine the risk before at least one of the one or more subjects is even treated for the respective condition, at some point during a period of time over which at least one of the one or more subjects is being treated for the respective condition, or after at least one of the one or more subject has completed treatment for the respective condition (but before the expiration of the respective retreatment time periods for all of the one or more subjects).

And the computing apparatus may subsequently re-determine and refine the risk one or more times before the expiration of the coverage period and before the expiration of all of the retreatment time periods.

Furthermore, the one or more subjects may be patients of a single treatment provider, or of multiple treatment providers, or at least one of the one or more subjects may have a non-patient relationship to the respective treatment provider. An example of the former includes a company that owns multiple hospitals, and the risk is determined for subjects receiving treatment at any of these hospitals. And an example of the latter is where the at least one of the one or more subjects is a participant in a clinical trial. And although an embodiment of the method described in conjunction with FIG. 5 contemplates human subjects, the concepts described in this disclosure may also apply to non-human subjects, such as pets or racehorses.

Moreover, examples of treatments that the one or more subjects may receive, conditions for which the one or more subjects may receive such treatments, retreatments that the one or more subjects may receive, and retreatment time periods, are described above in conjunction with FIG. 1.

In addition, determining a risk that one or more subjects will be retreated can include determining a risk that one or more subjects over and above a threshold number of subjects will be retreated. For example, the computing apparatus may determine the risk that more than a percentage (e.g., 1%, 2%, or 3%) of subjects treated by a provider will be retreated. Determining the risk in this manner may be useful where a retreatment penalty kicks in if more than a threshold number of treated subjects are retreated within respective retreatment time periods.

Still referring to FIG. 5, and referring again to the step 84, the computing apparatus may calculate the fee by mathematically calculating, using statistics or other mathematical techniques, the fee in response to the risk determined at the step 82. For example, the computing apparatus may calculate the fee at any time after the risk is determined at the step 82, and the computing apparatus may subsequently recalculate or otherwise refine the fee one or more times before the expiration of the coverage period and of all of the one or more retreatment time periods.

Examples of the fee and of its possible structure are described above in conjunction with FIGS. 1 and 3.

Furthermore, examples of taking the respective action include paying money to a beneficiary of a retreatment contract, such as a retreatment insurance policy, partially or fully reimbursing the beneficiary for the cost of retreating at least one of the one or more subjects or for a penalty associated with retreating at least one of the one or more subjects, or surrendering an item or service of value. Alternatively, taking the respective action may include retreating at least one of the one or more subjects within the respective time period if, before the at least one subject is retreated, it is determined that the at least one subject requires retreatment or that the at least one subject should be retreated. Furthermore, taking the respective action may encompass taking multiple respective actions either together or separately for each subject that is retreated within the retreatment time period. Further examples of taking the action are described above in conjunction with FIGS. 1-4, where these examples can be modified for one or more subjects.

Still referring to FIG. 5, alternate embodiments of the method represented by the flow diagram 80 are contemplated. For example, the method may include steps in addition to the steps 82 and 84, may include only a single one of the steps 82 and 84, and one or both of the steps 82 and 84 may be modified. Furthermore, the computing apparatus may perform one or both of the steps 82 and 84 in a non-automatic manner, or in response to human or other intervention; alternatively another type of apparatus, or even a human, may perform one or both of these steps.

FIG. 6 is a flow diagram 90 of a method for managing a risk that one or more subjects each treated for a respective condition by respective provider will be retreated within a respective retreatment time period, according to another embodiment.

Referring to a step 92, a computing apparatus automatically receives information relative to a risk that one or more subjects each treated for a respective condition by a respective provider will be retreated for the respective condition, or for a respective other reason, within a respective retreatment time period. Examples of such information are described above in conjunction with FIG. 2. Additional examples of such information include the number (if known at the time that a retreatment contract is generated) of the one or more subjects to be covered, the threshold number (if any) of retreated subjects above which the risk is to be determined, the length and timing of the retreatment contract's coverage period, and whether "retreated" encompasses retreatment for any reason or only for the respective condition for which a respective subject was previously treated.

Then, referring to a step 94, which can be similar to the step 82 of FIG. 5, the computing apparatus automatically determines, in response to the information received at the step 92, the risk that the one or more subjects each treated for a respective condition by a respective provider will be retreated within a respective retreatment time period. As described above, "retreated" may encompass retreating a respective subject for any reason, or only for the respective condition (or complications arising from the respective condition or the retreatment thereof) for which the respective subject was previously treated.

Next, referring to a step 96, which can be similar to the step 84 of FIG. 5, the computing apparatus automatically calculates, in response to the risk determined in the step 24, a fee for taking a respective action for each of the one or more subjects that is retreated within the respective retreatment time period.

Then, referring to a step 98, the computing apparatus automatically generates a retreatment contract that includes at least one recital that a party is to pay the calculated fee, and that another party is to take the respective action for each of the one or more subjects that is retreated within the respective retreatment time period. For example, the computing apparatus may generate a retreatment contract that is similar to the retreatment contract 40 of FIG. 3, but with the recitals modified to reflect that the contract covers the retreatments of one or more subjects each treated for a respective condition. Furthermore, the computing apparatus may generate the retreatment contract in any suitable format, such as in electronic format or on paper via a printer coupled to, or part of, the computing apparatus.

Still referring to the step 98, the party that is obligated to pay the fee calculated at the step 26 can be a single person, multiple persons, or any one or more non-person entities such as a business or trust. Examples of the party include a buyer of a right under the retreatment contract, a beneficiary of the retreatment contract, an insured under the retreatment contract, and a treatment provider (e.g., a physician, hospital, medical clinic, or medical association) associated with treating at least one of the one or more subjects for a respective condition. Other examples of the party paying the fee are described above in conjunction with FIGS. 1-3.

The party that is obligated to take the respective action described above in conjunction with the steps 96 and 98 also can be a single person, multiple persons, or any one or more non-person entities such as a business or trust. Examples of the action-obligated party include an insurer (e.g., of a treatment provider) under the contract, a seller of a right under the contract (e.g., to the fee-paying party), at least one of the one or more subjects (e.g., the at least one subject may act as an insurer to the fee-paying party), and at least one treatment provider (e.g., a physician, hospital, medical clinic, or medical association) associated with treating or retreating at least one of the one or more subjects. Other examples of the party obligated to take the respective action are described above in conjunction with FIGS. 1-3.

Still referring to the step 98, examples of taking the respective action, a respective retreatment of a respective subject, and the respective retreatment time period are described above in conjunction with the step 14 of FIG. 1.

Furthermore, after the computing apparatus generates the retreatment contract at the step 98, the computing apparatus may transfer the contract to a third party in a manner similar to that described above in conjunction with FIG. 4.

Next, referring to a step 100, the computing apparatus automatically receives information relative to the fee-paying party's and the action-obligated party's performance of their obligations under the retreatment contract. For example, the computing apparatus may receive such information in any suitable manner, such as from the internet via a local area network (LAN). Moreover, the computing apparatus may track the fee-paying party's payment of the fee calculated at the step 96, and may notify the action-obligated party (or other party) if the fee-paying party is late with a payment. The computing apparatus also may receive information indicating that at least one of the one or more subjects has been retreated within a respective retreatment period, and, in response to this information, may generate a notice to the action-obligated party that it needs to take the respective action specified in the retreatment contract. Furthermore, the computing apparatus may also track the action-obligated party, and may notify the fee-paying party if the action-obligated party does not take the respective action when it is obligated to do so under the contract.

Still referring to FIG. 6, alternate embodiments of the method represented by the flow diagram 90 are contemplated. For example, the method may include steps in addition to the steps 92-100, may omit one or more of the steps 92-100, or one or more of these steps may be modified. Furthermore, the computing apparatus may perform one or more of the steps 92-100 other than automatically, or in response to human or other intervention; or another type of apparatus, or even a human being, may perform one or more of these steps.

Referring again to FIG. 4, even though the computing apparatus can transfer a retreatment contract, such as the retreatment contract 40 of FIG. 3 or the retreatment contracts described above in conjunction with FIGS. 5-6, to an acquirer such as an investor, many potential acquirers may believe it is too risky to acquire a single retreatment contract. For example, suppose an investor wants to acquire the right to receive the payment(s) of the fee under a retreatment contract as an investment, but also must acquire the obligation to take an action if a subject is retreated. Because the cost of taking the action may far exceed the amount of the fee, the investor may be taking a relatively large risk that it will lose money on the investment if even one subject is retreated.

Consequently, to reduce its overall risk exposure, an investor may wish to acquire multiple retreatment contracts, the theory being that the payments from all of the contracts may exceed the costs for taking a respective action for one or more subjects that are retreated under these contracts.

But acquiring multiple retreatment contracts one by one may be tedious and otherwise uneconomical.

Furthermore, depending on the number and terms of the retreatment contracts acquired, the acquirer's overall risk exposure may not be that much smaller, and may even be the same or greater, than the overall risk exposure of a single retreatment contract.

Consequently, to reduce its overall risk, an investor may wish to balance its investment portfolio by acquiring a number of different types of instruments, including one or more retreatment contracts, that may each have a relatively high, or otherwise relatively unattractive, risk, but that together can have an aggregate risk that is relatively low, or otherwise relatively attractive.

Because many investors are not sophisticated enough to determine which, and how many, retreatment contracts and other instruments will provide a desired aggregate risk profile, an entity such as an investment company may package a number of such instruments together to form an asset having a defined risk profile and having shares that the entity can sell, or otherwise transfer, to one or more investors.

An asset that includes at least one retreatment contract, such as the retreatment contract 40 (FIG. 3) or the retreatment contracts described in conjunction with FIGS. 5-6, and methods related to the formation and transfer of such an asset, are described below in conjunction with FIGS. 7-10, according to an embodiment.

Figure 7:
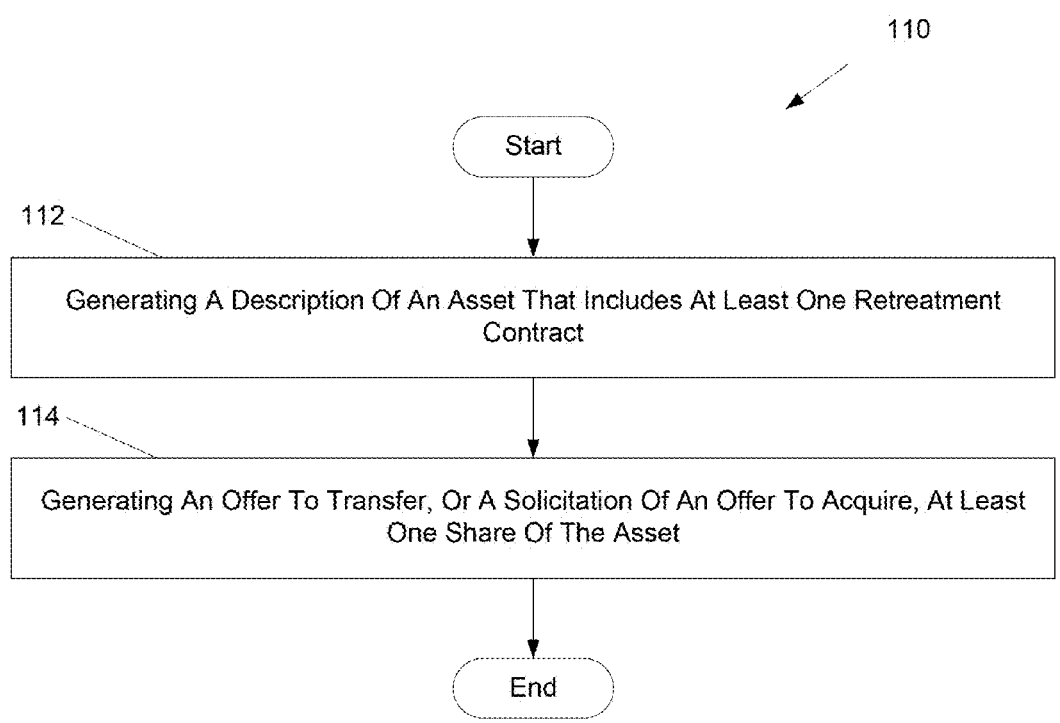
FIG. 7 is a flow diagram of a method for generating a description of, and an offer to transfer, an asset that includes at least one retreatment contract, according to an embodiment.

FIG. 7 is a flow diagram 110 of a method for generating a description of, and an offer to transfer or a solicitation of an offer to acquire, at least one share of an asset that includes at least one retreatment contract, according to an embodiment. For example, the asset may include at least one retreatment contract 40 of FIG. 3, or at least one of the retreatment contracts described above in conjunction with FIGS. 5-6.

Referring to a step 112, a computing apparatus automatically generates a description of an asset that includes at least one retreatment contract and at least one other instrument. The description may include the type(s) of retreatment contract(s) and other instruments included in the asset, and may include the rights and obligations of the parties to each contract and each instrument that are included in the asset. For example, the description may specify that the asset will receive payments of all fees under a retreatment contract, but will be obligated to pay a specified fraction, or a full amount, of the retreatment costs of any covered subject that is retreated (as "retreated" is defined in the retreatment contract) within a respective retreatment period. Furthermore, the description may include the number and classes of shares of the asset. Moreover, the computing apparatus may generate the description of the asset before or after the asset is formed. In addition, the computing apparatus may generate the description of the asset in any suitable format, such as on paper or in an electronic file.

Next, referring to a step 114, the computing apparatus automatically generates an offer to transfer, or a solicitation of an offer to acquire, at least one share of the asset that is the subject of the description generated at the step 112 above; for example, a solicitation of an offer may be made in a situation where the asset seller wants potential transferees to bid on shares of the asset. The offer or solicitation of an offer may include the generated description of the asset, and the share price for each share class of the asset. Furthermore, the computing apparatus may generate the offer to transfer, or the solicitation of an offer to acquire, at least one share of the asset before or after the asset is formed. Moreover, the computing apparatus may generate the offer to transfer, or the solicitation of an offer to acquire, at least one share of the asset in any suitable format, such as on paper or in an electronic file.

Still referring to FIG. 7, alternate embodiments of the method represented by the flow diagram 110 are contemplated. For example, the method may include steps in addition to the steps 112-114, may omit one of the steps 112-114, and one or more of these steps may be modified. Furthermore, the computing apparatus may perform one or more of the steps 112-114 other than automatically, or in response to human or other intervention; or another type of apparatus, or even a human being, may perform one or more of these steps. Moreover, the computing apparatus may automatically repeat the step 114 as appropriate to make multiple offers or multiple solicitations of offers.

Figure 8:
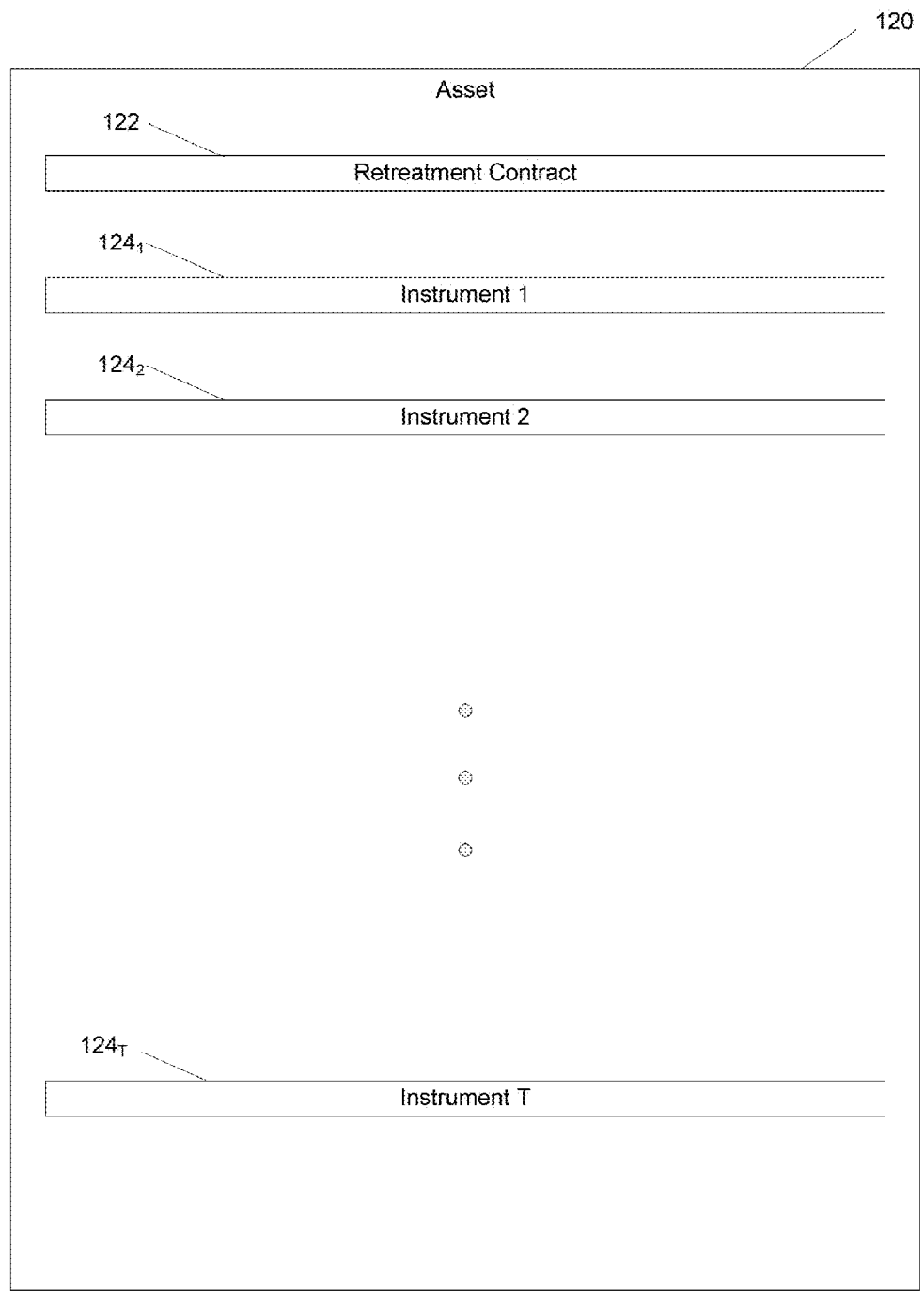
FIG. 8 is a diagram of an asset that includes at least one retreatment contract, such as the retreatment contract of FIG. 3, according to an embodiment.

FIG. 8 is a diagram of an asset 120 that includes at least one retreatment contract 122, according to an embodiment. For example, the retreatment contract 122 may be similar to the retreatment contract 40 of FIG. 3, or similar to one of the retreatment contracts described in conjunction with FIGS. 5-6. And in addition to the at least one retreatment contract 122, the asset 120 may include at least one other instrument $124_1$-$124_T$, where T≥1.

Examples of the asset 120 include a pooled asset, bundled asset, collateralized asset, and over-collateralized asset, which are further described below in conjunction with FIG. 10, and any other asset that can include at least one retreatment contract and at least one other instrument.

And examples of the at least one instrument 124 include a financial instrument, negotiable instrument, another contract such as an insurance policy, another retreatment contract, and any other type of instrument that can be combined with at least one retreatment contract to form the asset 120. If the at least one instrument 124 includes one or more retreatment contracts other than the retreatment contract 122, then these one or more other retreatment contracts may include one or more terms that are different than the respective terms of the retreatment contract 122. For example, the one or more other retreatment contracts may identify different subjects, different parties, different beneficiaries, different conditions, different fees, different coverage periods, different actions to be taken, different limitations on transferring rights or obligations under the contract, or different retreatment periods relative to the retreatment contract 122.

Figure 9:
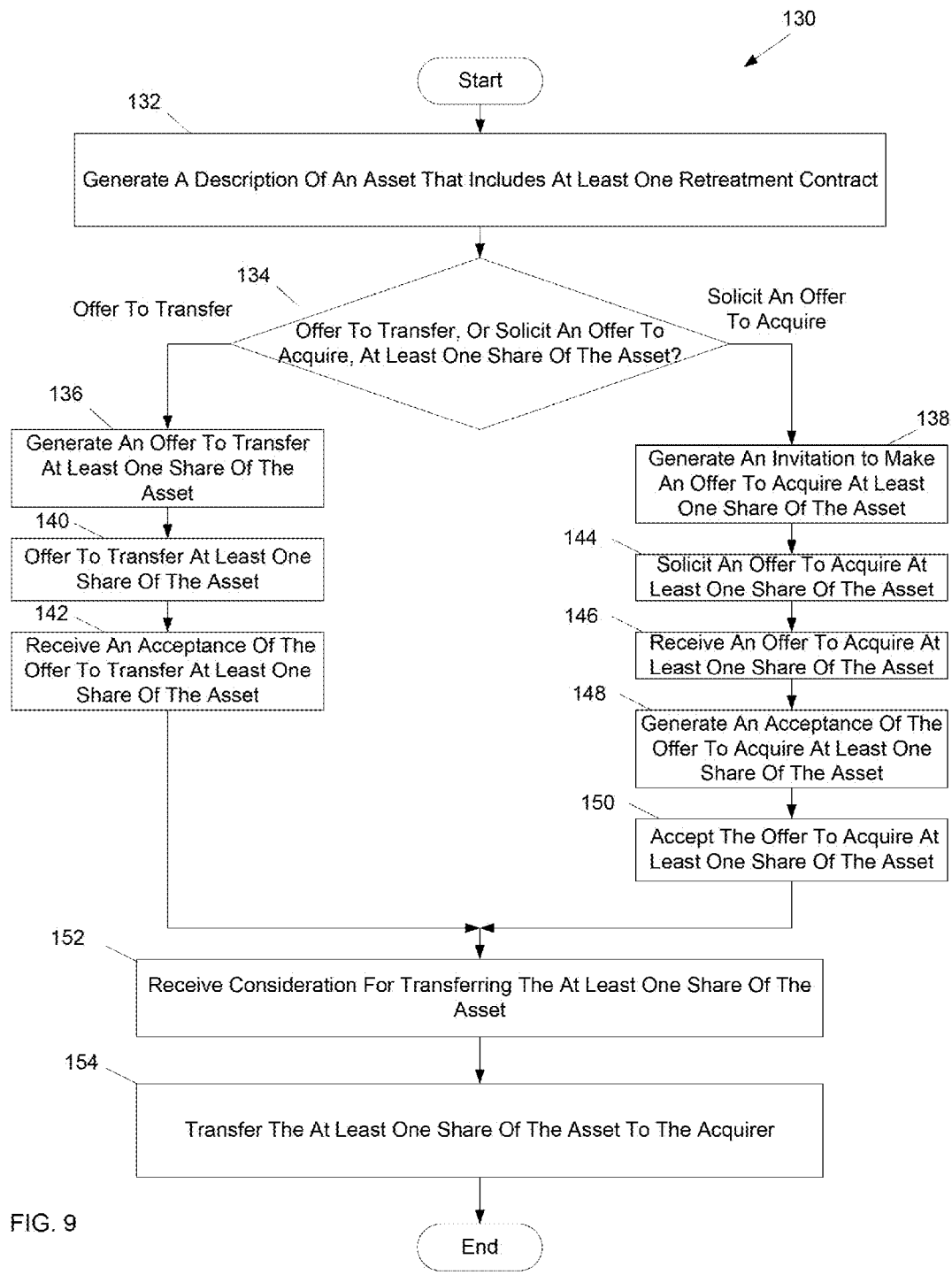
FIG. 9 is a flow diagram of a method for generating a description of, and managing a transfer of, an asset, such as the asset of FIG. 8, according to an embodiment.

FIG. 9 is a flow diagram 130 of a method for generating a description of, and managing a transfer of, an asset that includes at least one retreatment contract, according to an embodiment. For example, the asset may be, or may be similar to, the asset 120 of FIG. 8. Hereinafter, terms such as "transferring the asset," "selling the asset," "transferring shares in the asset," and "selling shares in the asset" refer to the transfer/sale to one or more third parties one or more shares of one or more rights or obligations under the items (e.g., at least one retreatment contract and at least one other instrument) that form the asset, where the transfer may, or may not, be for return consideration. For example, shares of the asset 120, which include shares of the right to receive the fee under the retreatment contract, may be sold to one or more investors.

Referring to a step 132, a computing apparatus automatically generates a description of an asset that includes at least one retreatment contract, such as the one retreatment contract 122 of FIG. 8, according to an embodiment; the asset may also include at least one other instrument, such as another instrument 124 of FIG. 8. Details of this step may be similar to those described above in conjunction with the step 112 of FIG. 7.

Next, referring to a step 134, the computing apparatus automatically determines whether to offer at least one share of the asset for transfer or to solicit an offer to acquire at least one share of the asset.

If, at the step 134, the computing apparatus "decides" to offer at least one share of the asset 120 for transfer, then the computing apparatus proceeds to a step 136; otherwise, the computing apparatus proceeds to a step 138.

Referring to the step 136, the computing apparatus automatically generates an offer to transfer at least one share of the asset, where the generated offer may be in any suitable format such as paper or electronic format. For example, the computing apparatus may generate an offer to transfer to a third party one or more shares that, at least in part, grant the shareholder the right to receive the fee (e.g., an insurance premium paid on a monthly basis) that a party pays under a retreatment contract that forms at least part of the asset.

Next, referring to a step 140, the computing apparatus automatically makes an offer to transfer at least one share of the asset. For example, the computing apparatus may cause the offer generated at the step 140 to be published in an online investment market place, or may send the offer directly to potential acquirers, for example, investment houses.

Then, referring to a step 142, the computing apparatus automatically receives an acceptance of the offer to transfer at least one share of the asset. For example, the computing apparatus may receive the acceptance from the accepting party in an email, text, voice communication, or other electronic communication received via the internet or a phone system.

But if the computing apparatus instead "decides" at the step 134 to solicit an offer to acquire at least one share of the asset instead of offering to transfer at least one share of the asset, then, referring to the step 138, the computing apparatus automatically generates an invitation to make an offer to acquire at least one share of the asset, where the generated invitation may be in any suitable format such as electronic or paper format. For example, the computing apparatus may generate an invitation to make an offer to acquire one or more shares of the right of a party under a retreatment contract of the asset to receive the fees paid by another party to the retreatment contract.

Next, referring to a step 144, the computing apparatus automatically solicits an offer to acquire at least one share of the asset. For example, the computing apparatus may cause the invitation generated at the step 138 to be published in an online investment market place, or may send the offer directly to potential acquirers for example, investment houses. Furthermore, the invitation may solicit competitive bidding (secret or public) to acquire one or more shares of the asset.

Then, referring to a step 146, the computing apparatus automatically receives an offer to acquire at least one share of the asset. For example, the computing apparatus may receive the offer from the offering third party in an email, text, voice communication, or other electronic communication via the internet or a phone system. If the computing apparatus receives offers in the forms of bids, then the computing apparatus may automatically track the bids by, e.g., the bid amount and the number of shares bid on.

Next, referring to a step 148, the computing apparatus automatically generates an acceptance of the received offer to acquire at least one share of the asset, where the generated acceptance may be in any suitable format such as electronic or paper format.

Then, referring to a step 150, the computing apparatus automatically accepts the offer to acquire at least one share of the asset. For example, the computing apparatus may send the acceptance generated at the step 148 via email to the third party who made the offer.

Next, after whichever of the step 142 and the step 150 that the computing apparatus performs, referring to a step 152, the computing apparatus automatically receives consideration from the acquirer for transferring the at least one share of the asset. For example, the computing apparatus may receive an electronic payment from the credit card, debit card, or bank account of the acquirer. And if the acquirer is obligated to make one or more future payments (e.g., monthly installments), then the computing apparatus may also receive these payments in due course.

Then, referring to a step 154, the computing apparatus transfers the at least one share of the asset to the acquirer. For example, the computing apparatus may generate and send to the acquirer a share certificate that memorializes the details of the transfer.

Still referring to FIG. 9, alternate embodiments of the method represented by the flow diagram 130 are contemplated. For example, the method may include steps in addition to the steps 132-154, may omit one or more of the steps 132-154, or may modify one or more of these steps. Furthermore, the computing apparatus may perform one or more of the steps 132-154 other than automatically, or in response to human or other intervention; or another type of apparatus, or even a human, may perform one or more of these steps. Moreover, the computing apparatus may automatically repeat one or more of the steps 132-154 as appropriate to make multiple offers, multiple solicitations of offers, multiple acceptances, or multiple share transfers.

Figure 10:
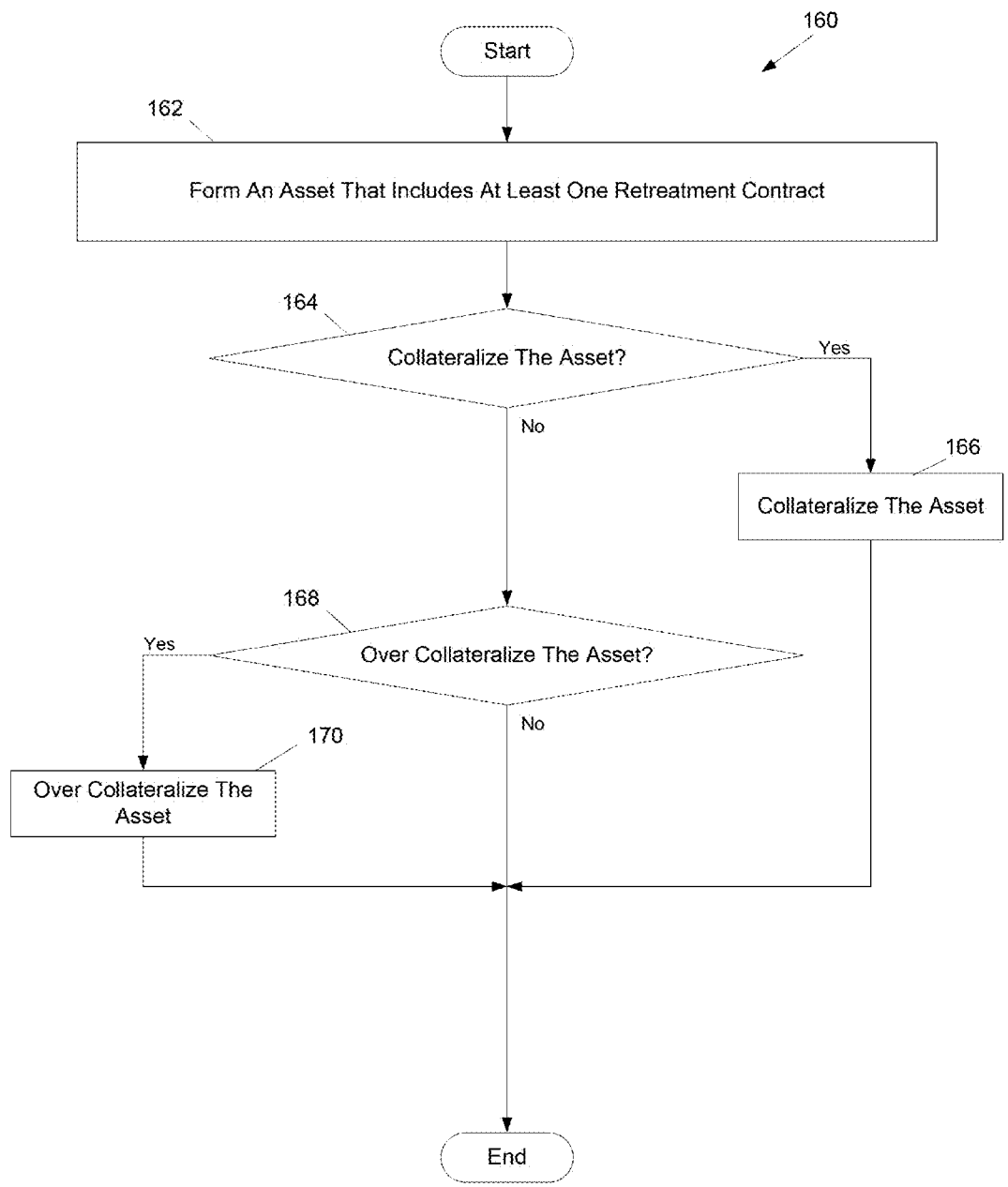
FIG. 10 is a flow diagram of a method for forming an asset, such as the asset of FIG. 8, according to an embodiment.

FIG. 10 is a flow diagram 160 of a method for forming an asset, such as the asset 120 of FIG. 8, according to an embodiment.

Referring to a step 162, a computing apparatus automatically forms an asset, such as the asset 120 of FIG. 8, that includes at least one retreatment contract (e.g., the retreatment contract 122 of FIG. 8), and that may also include at least one other instrument (e.g., such as the other instruments 124 of FIG. 8). For example, the computing apparatus may automatically generate the documents that need to be filed to form the asset legally, and then may automatically file these documents with the proper entity or entities (e.g., a government agency such as the Securities and Exchange Commission) to form the asset. Such documents may include a description of the asset, which description the computing apparatus may generate as described above in conjunction with step 112 of FIG. 7 and step 132 of FIG. 9. And where the asset is to include more than one item (e.g., a retreatment contract and another instrument), then the computing apparatus may form the asset by pooling, bundling, or otherwise combining these items into the asset.

Next, referring to a step 164, the computing apparatus determines whether the formed asset is to be collateralized. If the computing apparatus determines that the formed asset is to be collateralized, then it proceeds to a step 166; otherwise, the computing apparatus proceed to a step 168.

Referring to the step 166, the computing apparatus automatically collateralizes the formed asset. Examples of collateralizing the formed asset include acquiring property such as bonds or other securities, and pledging this property as collateral, e.g., against a failure of a payment obligation on at least one of the items (e.g., one or more retreatment contracts and one or more other instruments) that forms the asset. Or, the computing apparatus may make the pledged property a part of the asset.

Alternatively, referring to the step 168, if the computing apparatus determines that the formed asset is not to be collateralized, then the computing apparatus determines whether the formed asset is to be over-collateralized. If the computing apparatus determines that the formed asset is to be over-collateralized, then it proceeds to a step 170; otherwise, the computing apparatus ends the process such that the formed asset is neither collateralized nor over-collateralized.

Referring to the step 170, the computing apparatus automatically over-collateralizes the formed asset. Examples of over-collateralizing the formed asset include acquiring property such as bonds or other securities, and pledging this property as collateral, e.g., against a failure of a payment obligation on at least one of the items (e.g., one or more retreatment contracts and one or more other instruments) that form the asset, where the value of the property (or its payout) is greater than the value (or payout) of the items. Or, the computing apparatus may make the pledged property a part of the asset.

At the end of the asset-formation method, the formed asset is uncollateralized, collateralized, or over-collateralized.

Still referring to FIG. 10, alternate embodiments of the method represented by the flow diagram 160 are contemplated. For example, the method may include steps in addition to the steps 162-170, may omit one or more of the steps 162-170, or may modify one or more of these steps. Furthermore, the computing apparatus may perform one or more of the steps 162-170 other than automatically, or in response to human or other intervention; or another type of apparatus, or even a human, may perform one or more of these steps.

Referring to FIGS. 7-10, to further reduce the risk profile, and to further increase the attractiveness, of an investment beyond the risk profile and attractiveness of a single asset such as the asset 120 of FIG. 8, a computing apparatus can automatically form an entity that includes one or more assets, such as one or more of the asset 120 of FIG. 8 or of a similar asset.

Figure 11:
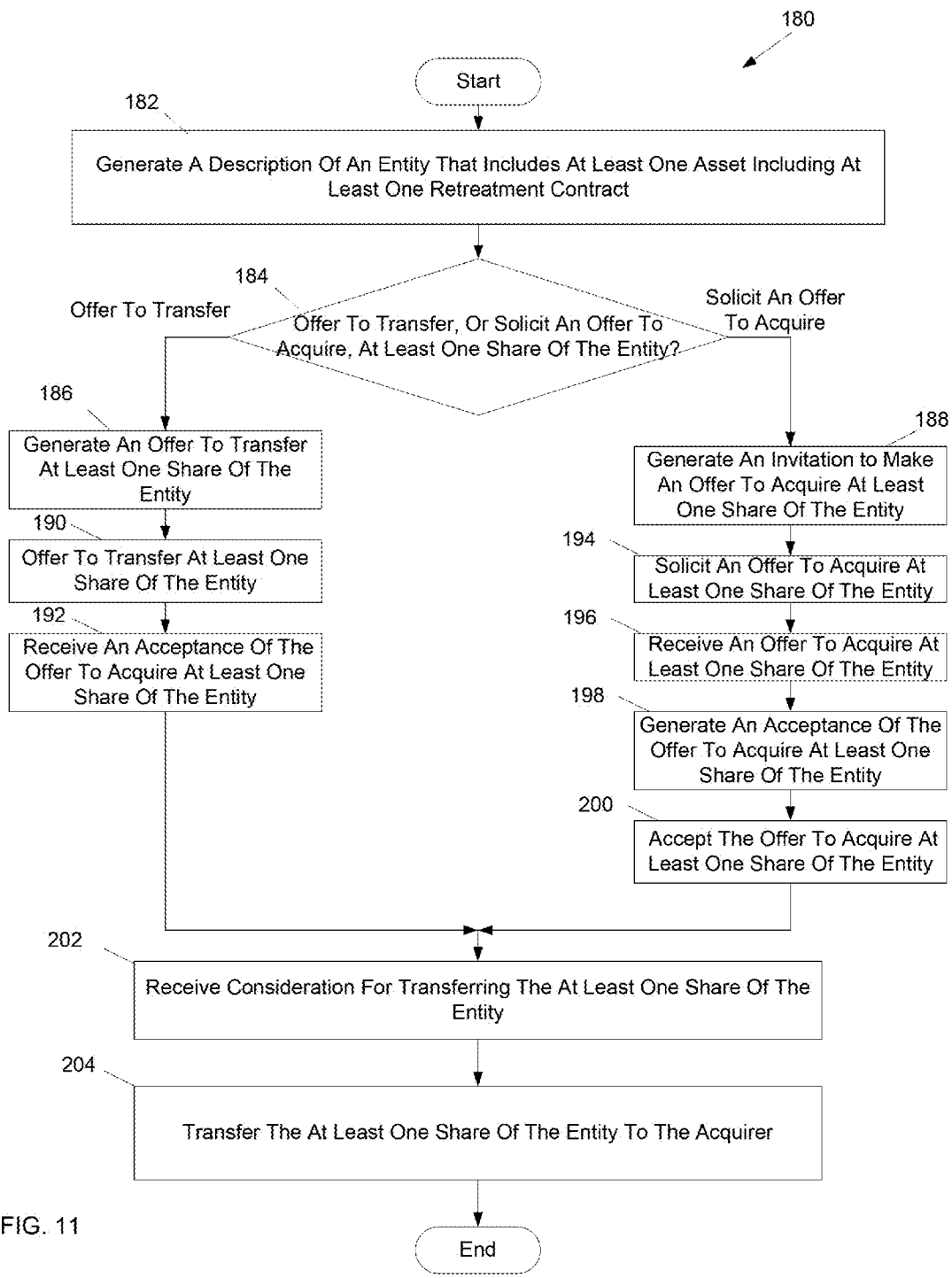
FIG. 11 is a flow diagram of a method for generating a description of an entity that includes an asset, such as the asset of FIG. 8, and for managing a transfer of one or more shares of the entity, according to an embodiment.

FIG. 11 is a flow diagram 180 of a method for generating a description of an entity that includes at least one an asset (e.g., the asset 120 of FIG. 8) that includes at least one retreatment contract (e.g., the retreatment contract 122 of FIG. 8 or the retreatment contract 40 of FIG. 3), and for managing a transfer of one or more shares of the entity, according to an embodiment. As described below in conjunction with FIGS. 12-14, the described entity may be, e.g., a pass-through entity, a special-purpose entity, or an entity that includes tranches. Furthermore, hereinafter, terms such as "transferring the entity," "selling the entity," "transferring shares in the entity," and "selling shares in the entity" refer to the transfer/sale of one or more shares of one or more rights or obligations under the assets that form the entity to one or more third parties, where the transfer may, or may not, be for return consideration. For example, shares of the entity, which include shares of the right to receive a fee under an asset that forms part of the entity, may be sold to one or more investors. Moreover, the entity may also include one or more assets that do not include a retreatment contract.

Referring to a step 182, a computing apparatus automatically generates a description of an entity that includes at least one asset (e.g., the asset 120 of FIG. 8) including at least one retreatment contract (e.g., the retreatment contract 122 (FIG. 8) or the retreatment contract 40 of FIG. 3), and that may include at least one other asset, according to an embodiment. The computing apparatus may generate the description of the entity in any suitable format, such as in electronic format or on paper via a printer coupled to, or part of, the computing apparatus.

Next, referring to a step 184, the computing apparatus automatically determines whether to offer at least one share of the entity for transfer or to solicit an offer to acquire at least one share of the entity.

If, at the step 184, the computing apparatus "decides" to offer at least one share of the entity for transfer, then the computing apparatus proceeds to a step 186; otherwise, the computing apparatus proceeds to a step 188.

Referring to the step 186, the computing apparatus automatically generates an offer to transfer at least one share of the entity, where the generated offer may be in any suitable format such as paper or electronic format. For example, the computing apparatus may generate an offer to transfer to a third party one or more shares that, at least in part, grant the shareholder the right to receive the fee (e.g., an insurance premium paid on a monthly basis) that a party pays under a retreatment contract that forms at least part of at least one asset of the entity.

Next, referring to a step 190, the computing apparatus automatically makes an offer to transfer at least one share of the entity. For example, the computing apparatus may cause the offer generated at the step 186 to be published in an online investment market place, or may send the offer directly to potential acquirers, for example, investment houses.

Then, referring to a step 192, the computing apparatus receives an acceptance of the offer to acquire at least one share of the entity. For example, the computing apparatus may receive the acceptance from the accepting party in an email, text, voice communication, or other electronic communication received via the internet or a phone system.

But if the computing apparatus instead "decides" at the step 184 to solicit an offer to acquire at least one share of the entity instead of offering to transfer at least one share of the entity, then, referring to the step 188, the computing apparatus automatically generates an invitation to make an offer to acquire at least one share of the entity, where the generated invitation may be in any suitable format such as electronic or paper format. For example, the computing apparatus may generate an invitation to make an offer to acquire one or more shares of the right of a party of a retreatment contract of an asset that forms part of the entity to receive the fee (e.g., insurance premiums paid on a monthly basis) paid by another party.

Next, referring to a step 194, the computing apparatus automatically solicits an offer to acquire at least one share of the entity. For example, the computing apparatus may cause the invitation generated at the step 188 to be published in an online investment market place, or may send the offer directly to potential acquirers, for example, investment houses. Furthermore, the invitation may solicit competitive bidding (secret or public) to acquire one or more shares of the entity.

Then, referring to a step 196, the computing apparatus receives an offer to acquire at least one share of the entity. For example, the computing apparatus may receive the offer from the offering third party in an email, text, voice communication, or other electronic communication via the internet or a phone system.

Next, referring to a step 198, the computing apparatus automatically generates an acceptance of the received offer to acquire at least one share of the entity, where the generated acceptance may be in any suitable format such as electronic or paper format.

Then, referring to a step 200, the computing apparatus automatically accepts the offer to acquire at least one share of the entity. For example, the computing apparatus may send the acceptance generated at the step 198 via email to the third party who made the offer.

Next, after whichever of the step 192 and the step 200 that the computing apparatus performs, referring to a step 202, the computing apparatus automatically receives consideration from the acquirer for transferring the at least one share of the entity. For example, the computing apparatus may receive an electronic payment from the credit card, debit card, or bank account of the acquirer. And if the acquirer is obligated to make one or more future payments (e.g., monthly installments), then the computing apparatus may also receive these payments in due course.

Then, referring to a step 204, the computing apparatus automatically transfers the at least one share of the entity to the acquirer. For example, the computing apparatus may generate and send to the acquirer a transfer agreement or a share certificate that memorializes the details of the transfer.

Still referring to FIG. 11, alternate embodiments of the method represented by the flow diagram 180 are contemplated. For example, the method may include steps in addition to the steps 182-204, may omit one or more of the steps 182-204, or may modify one or more of these steps. Furthermore, the computing apparatus may perform one or more of the steps 182-204 other than automatically, or in response to human or other intervention; or another type of apparatus, or even a human, may perform one or more of these steps. Moreover, the computing apparatus may automatically repeat one or more of the steps 182-204 as appropriate to make multiple offers, multiple solicitations of offers, multiple acceptances, or multiple share transfers.

Figure 12:
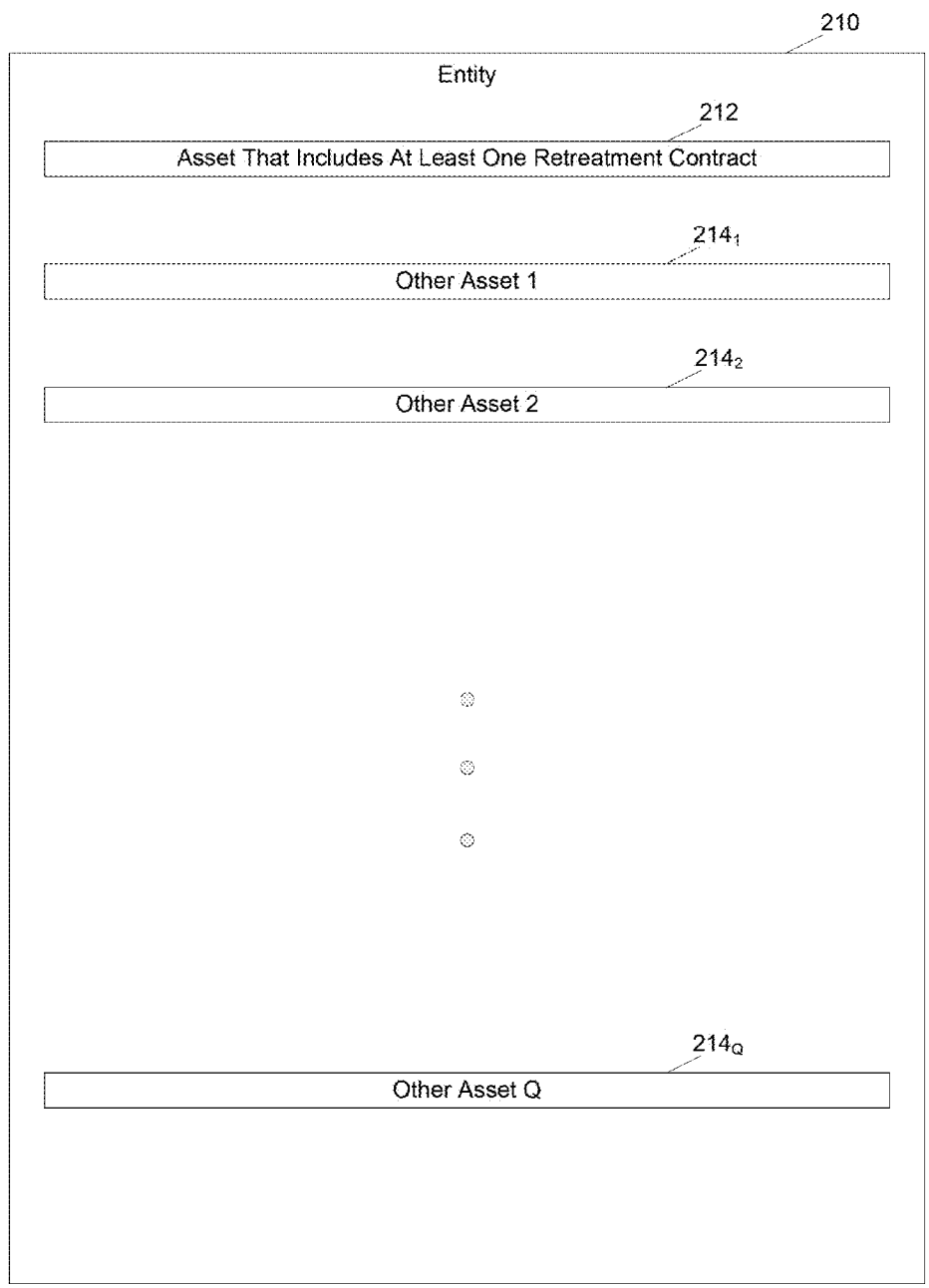
FIG. 12 is a diagram of an entity that includes an asset, such as the asset of FIG. 8, according to an embodiment.

FIG. 12 is a diagram of an entity 210 that includes at least one asset 212 that includes at least one retreatment contract, according to an embodiment. For example, the asset 212 may be the same as, or similar to, the asset 120 of FIG. 8, and the retreatment contract may be similar to, or the same as, the retreatment contract 40 of FIG. 3 or the retreatment contract 122 of FIG. 8. And in addition to the at least one asset 212, the entity 210 may include at least one other asset $214_1$-$214_Q$, where $Q \geq 1$.

Examples of the entity 210 include a pass-through entity, a special-purpose entity, or a tranched entity.

An embodiment of a pass-through entity is an entity in which the income that the entity generates flows through to the investor shareholders such that the entity itself is not taxed (only the investor shareholders are taxed on the income that they receive from the entity).

An embodiment of a special-purpose entity (sometimes called a "special-purpose vehicle") is an entity set up, e.g., to isolate a firm that owns the entity from financial risk, to hide debt or ownership of the assets that form the entity, or to obscure relationships between different entities.

And an embodiment of a tranched entity is described below in conjunction with FIG. 13.

Figure 13:
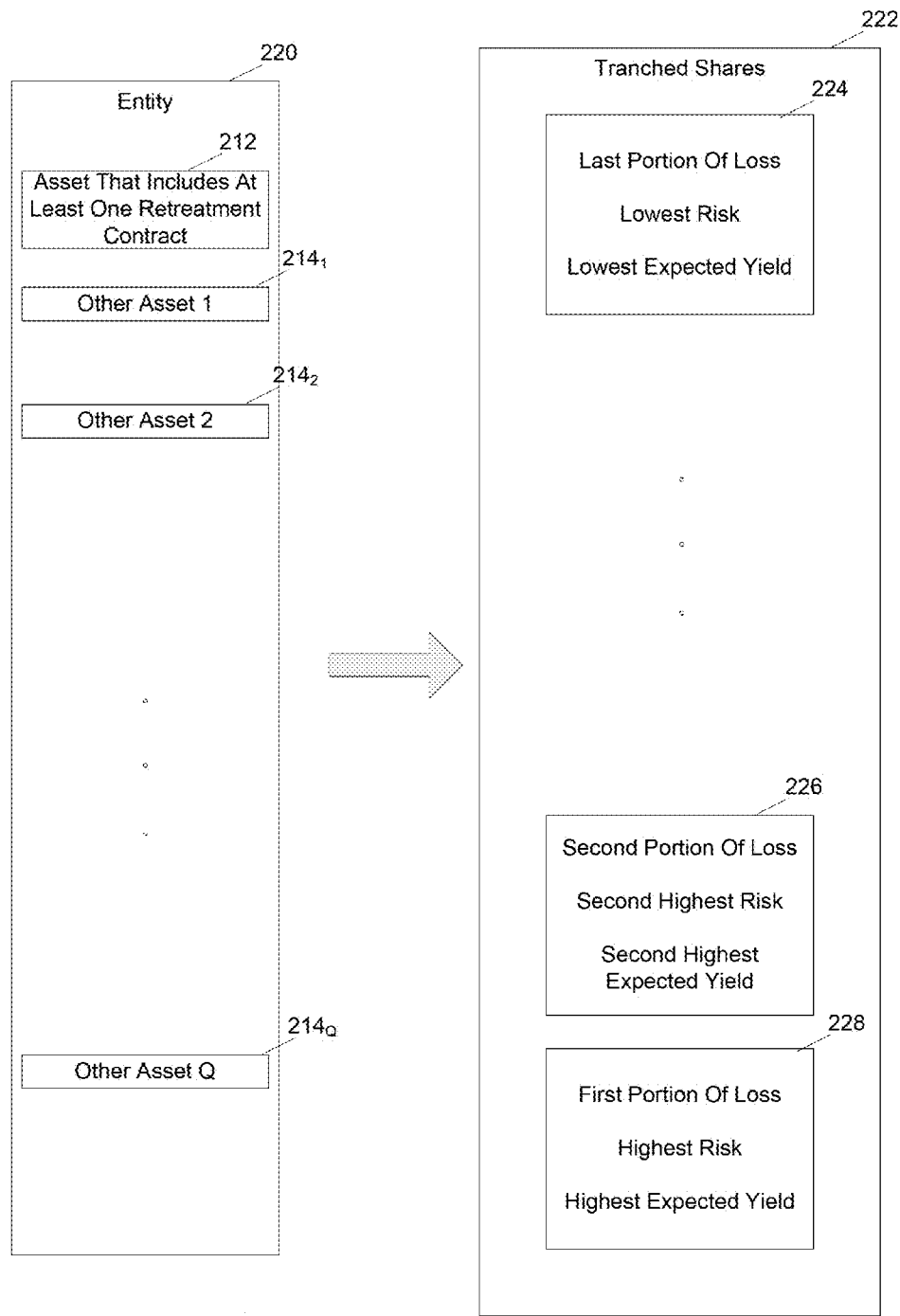
FIG. 13 is a diagram of the entity of FIG. 12, and of tranched share classes of the entity, according to an embodiment.

FIG. 13 is a diagram of a tranched entity 220, according to an embodiment in which the tranched entity includes the same asset(s), and thus has the same asset structure, as the entity 210 of FIG. 12. That is, like the entity 210, the entity 220 includes the asset 212, and may include at least one other asset $214_1$-$214_Q$, according to an embodiment.

The shares 222 of the entity 220 are tranched; that is, the shares are divided into different classes (only classes 224, 226, and 228 are shown, although the entity may include more or fewer than three share classes) each having a respective risk profile, a respective return profile, and a respective share price. For example, tranching allows the entity 220 to have different classes of shares, at least some of which may have a more attractive risk profile than the average risk profile of the underlying assets 212, and possibly one or more assets 214, that form the entity.

In an example, the entity 220 has three and only three classes 224, 226, and 228 of shares, and has a basis of US$90,000,000. The class 224 shares, as a group, absorb the last 33⅓% of any losses (relative to the basis) that the entity 220 experiences, and receive 20% of any profit that the entity earns. The class 226 shares, as a group, absorb the next 33⅓% of any losses that the entity 220 experiences, and receive 35% of any profit that the entity earns. And the class 228 shares, as a group, absorb the first 33⅓% of any losses that the entity 220 experiences, and receive 45% of any profit that the entity earns.

Continuing with this example regarding the sharing of a loss that the entity 220 suffers, if for example, the entity loses, e.g., via erosion of the asset values, US$25,000,000, then the group 228 shares absorb this entire loss, and the groups 224 and 226 shares suffer no loss. If the entity 220 loses US$50,000,000, then the group 228 shares absorb US$30,000,000 of this loss, the group 226 shares absorb US$20,000,000 of this loss, and the group 224 shares suffer no loss. And if the entity 220 loses US$70,000,000, then the shares of the groups 228 and 226 each absorb US$30,000,000 of this loss (for a total loss of US$60,000,000 absorbed by the groups 228 and 226), and the group 224 shares absorb only US$10,000,000 of this loss.

And continuing with the above example regarding the entity 220 returning a profit, if, for example, the entity returns US$10,000,000, then the class 228 shares, as a group, are entitled to US$4,500,000, the class 226 shares are entitled to US$3,500,000, and the class 224 shares are entitled to US$2,000,000.

Still referring to FIG. 13, alternate embodiments of the tranched entity 220 are contemplated. For example, the entity 220 may be tranched such that it includes at least one class of shares having both a lower risk profile and a higher return profile; for example, such a class of shares may be considered a preferred class of shares that are sold to institutional investors (e.g., a pension fund) who purchase at least a specified minimum number of these shares.

Figure 14:
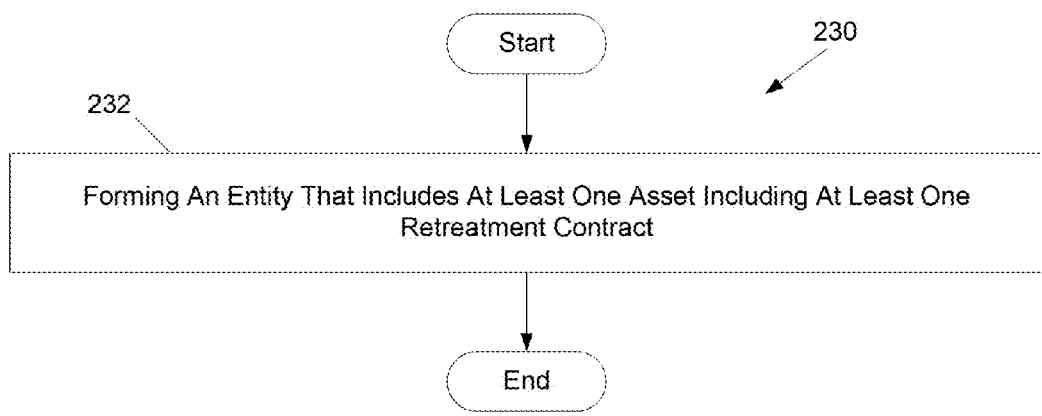
FIG. 14 is a flow diagram of a method for forming an entity, such as one of the entities of FIG. 12 and FIG. 13, according to an embodiment.

FIG. 14 is a flow diagram 230 of a method for forming an entity that includes at least one asset including at least one retreatment contract, according to an embodiment.

Referring to a step 232, a computing apparatus automatically forms an entity (e.g., the entity 210 of FIG. 12 or the tranched entity 220 of FIG. 13) that includes at least one asset (e.g., the asset 120 of FIG. 8 or the asset 212 of FIGS. 12 and 13) that includes at least one retreatment contract (e.g., the retreatment contract 40 of FIG. 3 or the retreatment contract 122 of FIG. 8). For example, the computing apparatus may automatically generate the documents that need to be filed to form the entity legally, and then may automatically file these documents with the proper authority or authorities (e.g., a government agency such as the Securities and Exchange Commission) to form the entity. Such documents may include a description of the entity, which description the computing apparatus may generate as described above in conjunction with step 112 of FIG. 7 or step 132 of FIG. 9. And where the entity is to include more than one asset, then the computing apparatus may form the entity by pooling, bundling, or otherwise combining these assets into the entity.

Still referring to FIG. 14, alternate embodiments of the method represented by the flow diagram 230 are contemplated. For example, the method may include steps in addition to the step 232, or may modify this step. Furthermore, the computing apparatus may perform the steps 232 other than automatically, or in response to human or other intervention; or another type of apparatus, or even a human, may perform this step.

FIG. 15 is a block diagram of a computing apparatus 240 that can automatically perform one or more steps of each of the methods described above in conjunction with FIGS. 1-2, 4-7, 9-11, and 14, according to an embodiment.

The computing apparatus 240 includes computing circuitry 242, which may be, or which may include, at least one microprocessor or at least one microcontroller. The computing circuitry 242 includes circuitry for performing various functions, such as executing specific software or implementing specific firmware to perform specific calculations or to control the computing apparatus 240 to provide a desired functionality; or, the computing circuitry may perform various functions solely in hardware, or in a combination or sub-combination of software, firmware, and hardware.

Furthermore, the computing apparatus 240 includes one or more input devices 244, such as a keyboard, mouse, touch screen, audible or voice-recognition component, and so on, coupled to the computing circuitry 242 to allow, e.g., an operator or other computer system, to interface with the other components of the computing apparatus.

Moreover, the computing apparatus 240 also includes one or more output devices 246 coupled to the computing circuitry 242, where the output devices can include a printer, a video display, an audio device (e.g., a speaker), a data-output device (e.g., a cable) and so on.

In addition, the computing apparatus 240 also includes one or more data-storage devices 248 that are coupled to the computing circuitry 242 to store data or to retrieve data from storage media (not shown). Examples of typical data-storage devices 248 include magnetic disks, FLASH memory, EPROMs, EEPROMS, and other types of solid-state memory, tape drives, optical disks like compact disks and digital versatile disks (DVDs), and so on.

Furthermore, the computing apparatus 240 may be part of a local-area network (LAN), and the computing circuitry 242 (or perhaps one or more other components of the computing apparatus) may be coupled to the internet directly or via the LAN, and, therefore, may be configured to send data to a remote receiver via the internet, and may be configured to receive data from a remote source via the internet.

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated.

While various aspects and embodiments have been disclosed herein, other aspects and embodiments will be apparent to those skilled in the art from the detailed description provided herein. The various aspects and embodiments disclosed herein are for purposes of illustration and are not intended to be limiting, with the true scope and spirit being indicated by the following claims.

What is claimed is:

1. A method, comprising:
    using a risk-determining circuit to determine automatically a risk that a subject medically treated for a medical condition will be medically retreated for the medical condition within a retreatment time period;
    using a fee-calculating circuit to calculate automatically, in response to a determined risk, a fee for taking an action if the subject is medically retreated for the medical condition within the retreatment time period;
    using a requesting circuit to request a first electronic to measure a biological condition of the subject at a first time, and to receive, from the first electronic device, a signal corresponding to the measured biological condition;
    using a determining circuit to determine, in response to the signal, whether the subject is adhering to a post-treatment regimen;
    if the first electronic device is unresponsive to the request, using requesting circuit to request a second electronic device associated with the first electronic device to request the first electronic device to measure a delayed biological condition of the subject while the second electronic device is within a communication range of the first electronic device, and to receive, from the second electronic device, a delayed signal corresponding to the measured delayed biological condition and a time difference between the first time and a second time at which the delayed biological condition is measured;
    using the determining circuit to generate, in response to the delayed signal and the time difference, an indication as to whether the subject is adhering to the post-treatment regimen;
    using the risk-determining circuit to update to update the risk in response to the indication; and
    using the fee-calculating circuit to update the fee in response to the updated risk.

2. The method of claim 1 wherein using the risk-determining circuit to determine the risk includes using the risk-determining circuit to determine the risk before the subject is treated for the condition.

3. The method of claim 1 wherein using the risk-determining circuit to determine the risk includes using the risk-determining circuit to determine the risk within a medical treatment period over which the subject is being medically treated for the medical condition.

4. The method of claim 1 wherein using the risk-determining circuit to determine the risk includes using the risk-determining to determine the risk after the subject is medically treated for the medical condition.

5. The method of claim 1 wherein using the risk-determining circuit to determine the risk includes using the risk-determining circuit to determine the risk that a subject admitted to a medical facility for medical treatment of the medical condition will be readmitted to the medical facility for medical retreatment of the medical condition within the retreatment time period.

6. The method of claim 1 wherein using the risk-determining circuit to determine the risk includes using the risk-determining circuit to determine the risk that a subject admitted to a medical facility for medical treatment of the medical condition will be admitted to another medical facility for medical retreatment of the medical condition within the retreatment time period.

7. The method of claim 1 wherein using the risk-determining circuit to determine the risk includes using the risk-determining circuit to determine a probability that the subject will be medically retreated for the medical condition within the retreatment time period.

8. The method of claim 1 wherein the fee includes an insurance premium.

9. The method of claim 1 wherein taking the action includes paying money to a beneficiary.

10. The method of claim 1 wherein taking the action includes reimbursing a beneficiary for a cost of retreatment.

11. The method of claim 1 wherein taking the action includes medically retreating the subject for the medical condition.

12. The method of claim 1, further comprising:
    using an information-receiving circuit to receive information about the subject; and
    wherein using the risk-determining circuit to determine automatically the risk includes using the risk-determining circuit to determine automatically the risk in response to the information.

13. The method of claim 1, further comprising:
    using an information-receiving circuit to receive information about the medical condition; and
    wherein using the risk-determining circuit to determine automatically the risk includes using the risk-determining circuit to determine automatically the risk in response to the information.

14. The method of claim 1, further comprising:
    using an information-receiving circuit to receive information about a medical treatment for the medical condition; and
    wherein using the risk-determining circuit to determine automatically the risk includes using the risk-determining circuit to determine automatically the risk in response to the information.

15. The method of claim 1, further comprising:
using an information-receiving circuit to receive information about the retreatment time period; and
wherein using the risk-determining circuit to determine automatically the risk includes using the risk-determining circuit to determine automatically the risk in response to the information.

16. The method of claim 1, further comprising:
using an information-receiving circuit to receive information about a medical facility for medically treating the subject for the medical condition; and
wherein using the risk-determining circuit to determine automatically the risk includes using the risk-determining circuit to determine automatically the risk in response to the information.

17. The method of claim 1, further comprising:
using an information-receiving circuit to receive information about a post-medical-treatment regimen for the subject; and
wherein using the risk-determining circuit to determine automatically the risk includes using the risk-determining circuit to determine automatically the risk in response to the information.

18. The method of claim 1, further comprising:
using an information-receiving circuit to receive information about a medical-treatment provider for the subject; and
wherein using the risk-determining circuit to determine automatically the risk includes using the risk-determining circuit to determine automatically the risk in response to the information.

19. The method of claim 1, further comprising using a contract-generating circuit to generate a medical retreatment contract that includes at least one recital that a party is to pay the fee and that another party is to take the action if the subject is medically retreated for the medical condition within the retreatment time period.

20. The method of claim 19 wherein the retreatment contract includes an insurance policy.

21. The method of claim 19 wherein the party includes an insured.

22. The method of claim 1, further comprising
using a contract-generating circuit to generate a medical-retreatment contract that includes at least one recital that a party is to pay the fee and that another party is to take the action if the subject is medically retreated for the medical condition within the retreatment time period; and
using an asset-forming circuit to form an asset that includes the medical-retreatment contract and at least one other negotiable instrument.

23. The method of claim 1, further comprising:
using a contract-generating circuit to generate a medical retreatment contract that includes at least one recital that a party is to pay the fee and that another party is to take the action if the subject is medically retreated for the medical condition within the retreatment time period; and
using an offer-generating circuit to generate an offer to sell the medical-retreatment contract.

24. An apparatus, comprising:
a determiner circuit configured to determine automatically a risk that a subject medically treated for a medical condition will be medically retreated for the medical condition within a retreatment time period;
a calculator circuit configured to calculate automatically, in response to a determined risk, a fee for taking an action if the subject is medically retreated for the medical condition within the retreatment time period;
a requester circuit configured to request a first electronic device to measure a biological condition of the subject at a first time, to receive, from the first electronic device, a signal corresponding to the measured biological condition, and configured, if the first electronic device is unresponsive to the request, to request a second electronic device associated with the first electronic device to request the first electronic device to measure a delayed biological condition of the subject while the second electronic device is within a communication range of the first electronic device, and to receive, from the second electronic device, a delayed signal corresponding to the measured delayed biological condition and a time difference between the first time and a second time at which the delayed biological condition is measured;
an analyzer circuit configured to determine, in response to the signal, or in response to the delayed signal and the time difference, whether the subject is adhering to a post-treatment regimen;
wherein the determiner circuit is further configured to update the risk in response to a determination as to whether the subject is adhering to the post-treatment regimen; and
wherein the calculator circuit is configured to update the fee in response to the updated risk.

25. The apparatus of claim 24 wherein the retreatment time period begins after the subject finishes a medical treatment for the medical condition.

26. An apparatus, comprising:
means for automatically determining a risk that a subject medically treated for a medical condition will be medically retreated for the medical condition within a retreatment time period; and
means for automatically calculating, in response to a determined risk, a fee for taking an action if the subject is medically retreated for the medical condition within the retreatment time period;
means for requesting a first electronic device to measure a biological condition of the subject at a first time;
means for receiving, from the first electronic device, a signal corresponding to the measured biological condition;
means for requesting, if the first electronic device is unresponsive to the request, a second electronic device associated with the first electronic device to request the first electronic device to measure a delayed biological condition of the subject while the second electronic device is within a communication range of the first electronic device;
means for receiving, from the second electronic device, a delayed signal corresponding to the measured delayed biological condition and a time difference between the first time and a second time at which the delayed biological condition is measured;
means for determining, in response to the signal, or in response to the delayed signal and the time difference, whether the subject is adhering to a post-treatment regimen;
means for updating the risk in response to a determination as to whether the subject is adhering to the post-treatment regimen; and
means for updating the fee in response to the updated risk.

27. The apparatus of claim 26, further comprising means for generating a medical-retreatment contract that includes:

at least one recital that a party is to pay the fee and that another party is to take the action if the subject is medically retreated for the medical condition within the retreatment time period; and at least one recital that the subject is to undergo a post-medical-treatment regimen.

28. A non-transitory computer-readable medium comprising:

stored instructions that, when executed by at least one computing apparatus, cause the at least one computing apparatus to determine automatically a risk that a subject medically treated for a medical condition will be medically retreated for the medical condition within a retreatment time period;

to calculate automatically, in response to the risk, a fee for taking an action if the subject is medically retreated for the medical condition within the retreatment time period;

to request a first electronic device to measure a biological condition of the subject at a first time;

to receive from the first electronic device a signal corresponding to the measured biological condition;

if the first electronic device is unresponsive to the request, to request a second electronic device associated with the first electronic device to request the first electronic device to measure a delayed biological condition of the subject while the second electronic device is within a communication range of the first electronic device;

to receive, from the second electronic device, a delayed signal corresponding to the measured delayed biological condition and a time difference between the first time and a second time at which the delayed biological condition is measured;

to determine, in response to the signal, or in response to the delayed signal and the time difference, whether the subject is adhering to a post-treatment regimen;

to update the risk in response to a determination as to whether the subject is adhering to the post-treatment regimen; and to update the fee in response to the updated risk.

29. The non-transitory computer-readable medium of claim 28 wherein the stored instructions, when executed by at least one computing apparatus, cause the at least one computing apparatus to generate a medical-retreatment contract that includes:

at least one recital that a party is to pay the fee and that another party is to take the action if the subject is medically retreated for the medical condition within the retreatment time period; and at least one recital that another party is to monitor the subject after the subject finishes being medically treated.

* * * * *

UNITED STATES PATENT AND TRADEMARK OFFICE
CERTIFICATE OF CORRECTION

PATENT NO. : 9,940,683 B2
APPLICATION NO. : 13/956128
DATED : April 10, 2018
INVENTOR(S) : Grace Hsu Huynh et al.

It is certified that error appears in the above-identified patent and that said Letters Patent is hereby corrected as shown below:

In the Claims

In Column 27, Line 66, Claim 1, "using the risk-determining circuit to update to update the" should read --using the risk-determining circuit to update the--

Signed and Sealed this
Second Day of October, 2018

Andrei Iancu
*Director of the United States Patent and Trademark Office*